US010517898B2

(12) United States Patent
Chute

(10) Patent No.: US 10,517,898 B2
(45) Date of Patent: Dec. 31, 2019

(54) COMPOSITIONS AND METHODS RELATED TO HEMATOLOGIC RECOVERY

(71) Applicant: The Regents of the University of California, Oakland, CA (US)

(72) Inventor: John P. Chute, Sherman Oaks, CA (US)

(73) Assignee: The Regents of the University of California, Oakland, CA (US)

( * ) Notice: Subject to any disclaimer, the term of this patent is extended or adjusted under 35 U.S.C. 154(b) by 4 days.

(21) Appl. No.: 15/528,355

(22) PCT Filed: Nov. 20, 2015

(86) PCT No.: PCT/US2015/061781
§ 371 (c)(1),
(2) Date: May 19, 2017

(87) PCT Pub. No.: WO2016/081808
PCT Pub. Date: May 26, 2016

(65) Prior Publication Data

US 2017/0319624 A1 Nov. 9, 2017

Related U.S. Application Data

(60) Provisional application No. 62/082,425, filed on Nov. 20, 2014.

(51) Int. Cl.

| | |
|---|---|
| ***A61K 35/28*** | (2015.01) |
| ***C12N 5/0789*** | (2010.01) |
| ***C12N 5/0775*** | (2010.01) |
| ***A61K 35/51*** | (2015.01) |
| *C12N 5/078* | (2010.01) |
| *A61K 35/12* | (2015.01) |

(52) U.S. Cl.
CPC .............. *A61K 35/28* (2013.01); *A61K 35/51* (2013.01); *C12N 5/0647* (2013.01); *C12N 5/0663* (2013.01); *C12N 5/0665* (2013.01); *A61K 2035/124* (2013.01); *C12N 2501/73* (2013.01)

(58) Field of Classification Search
None
See application file for complete search history.

(56) References Cited

U.S. PATENT DOCUMENTS

2012/0045459 A1 2/2012 MacKeigan et al.

FOREIGN PATENT DOCUMENTS

WO WO-2010/056332 A1 5/2010

OTHER PUBLICATIONS

Burman et al., "Regulation of autophagy by phosphatidylinositol 3-phosphate", FEBS Letters, vol. 584, pp. 1302-1312. (Year: 2010).*
Himburg et al., "Pleiotrophin Regulates the Expansion and Regeneration of Hematopoietic Stem Cells," Nat Med, 16(4): 475-482 (2010).
International Search Report and Written Opinion for International Application No. PCT/US2015/061781 dated Mar. 28, 2016.
Quarmyne et al., "Protein Tyrosine Phosphatase—Regulates Hemtopoietic Stem Cell—Repopulating Capacity," J Clin Invest, 125(1): 177 (2015).
Coşkun et al., "Development of the fetal bone marrow niche and regulation of HSC quiescence and homing ability by emerging osteolineage cells," Cell Rep, 9(2):581-590 (2014).
Dewang et al., "Protein tyrosine phosphatases and their inhibitors," Curr Med Chem, 12(1):1-22 (2005).
Extended European Search Report issued by the European Patent Office in corresponding Application No. EP 15861206.9, dated Apr. 24, 2018.

* cited by examiner

*Primary Examiner* — Michelle F. Paguio Frising
(74) *Attorney, Agent, or Firm* — Foley Hoag LLP

(57) ABSTRACT

In some aspects, the invention relates to populations of hematopoietic cells that are enriched in $PTP\sigma^-$ cells and methods of use thereof.

14 Claims, 12 Drawing Sheets

COMPOSITIONS AND METHODS RELATED TO HEMATOLOGIC RECOVERY

CROSS-REFERENCE TO RELATED APPLICATIONS

This application is a § 371 national-stage application based on PCT Application PCT/US2015/061781, filed Nov. 20, 2015, which claims the benefit of U.S. Provisional Application No. 62/082,425, filed on Nov. 20, 2014, the entire contents of each of which are incorporated by reference herein in their entirety.

GOVERNMENT SUPPORT

This invention was made with Government support under Grant No. AI067798, HL086998 awarded by the National Institutes of Health. The Government has certain rights in the invention.

SUMMARY OF THE DISCLOSURE

In some aspects, the invention relates to a mammalian population of cells comprising hematopoietic cells (HSCs) that are substantially free of cells that express protein tyrosine phosphatase sigma ("PTPσ") and methods of use thereof. In some embodiments, the cell population comprises a PTPσ inhibitor. In some aspects, a population of mammalian cells comprises HSCs and a PTPσ inhibitor. The PTPσ inhibitor may be a small molecule or an interfering nucleic acid (e.g., a siRNA, such as a shRNA). In some embodiments, the cell population is enriched in certain cell types, for example, in $CD34^+$, $CD38^-$, $CD45RA^-$, $CD90^+$, $lin^-$, $Rho^{lo}$, $CD49f^{+-}$, and/or $CD33^-$ cells. In other embodiments, the cell population is substantially free of certain cell types, such as CD34–, $CD38^+$, $CD45RA^+$, $CD90^-$, $lin^+$, $Rho^{hi}$, $CD49f^-$, and/or $CD33^+$ cells. The HSCs may be murine or human HSCs. The HSCs may be bone marrow or cord blood HSCs.

In some aspects, the invention provides a method for enriching the HSCs in a sample, including obtaining a sample of HSCs and removing $PTP\sigma^+$ cells from the sample.

In other aspects, the invention provides a method for implanting an effective amount of hematopoietic cells into a subject in need thereof, including obtaining the sample comprising hematopoietic cells, removing the $PTP\sigma^+$ cells from the sample, and implanting the sample into a subject. In some embodiments of these methods, the method includes contacting the sample with an anti-PTPσ antibody, and the $PTP\sigma^+$ cells are removed from the sample, e.g., by removing cells bound to the anti-PTPσ antibody. In some such embodiments, the anti-PTPσ antibody is labeled with a fluorophore and the cells are removed through fluorescence activated cell sorting. In other such embodiments, the anti-PTPσ antibody is labeled with a magnetic particle and cells are removed from the sample by exposing the sample to a magnetic field. In yet other such embodiments, the anti-PTPσ antibody is immobilized on a surface and cells are removed from the sample by separating the surface from the sample. In certain embodiments of these methods, the method comprises removing certain cell types, for example, CD34–, $CD38^+$, $CD45RA^+$, $CD90^-$, $lin^+$, $Rho^{hi}$, $CD49f^-$, and/or $CD33^+$ cells, from the sample.

In some aspects, the invention provides a method for producing a population of HSCs, including obtaining a sample comprising HSCs, sorting the cell in the sample based, at least in part, on their expression of PTPσ, and collecting the $PTP\sigma^-$ cells. In other aspects, the invention describes a method of implanting an effective amount of hematopoietic cells into a subject in need thereof, comprising obtaining a sample comprising hematopoietic cells, sorting the cells in the sample based, at least in part, on their expression of PTPσ, collecting the $PTP\sigma^-$ cells, and implanting the $PTP\sigma^-$ cells into the subject. In some embodiments of these methods, the method includes contacting the sample with an anti-PTPσ antibody, and sorting the cells, e.g., by collecting the cells in the sample that do not bind to the anti-PTPσ antibody. The anti-PTPσ antibody may be labeled with a fluorophore, and $PTP\sigma^-$ cells collected through fluorescence activated cell sorting. In other embodiments, the anti-PTPσ antibody may be labeled with a magnetic particle and $PTP\sigma^-$ cells collected by exposing the sample to a magnetic field. In yet other embodiments, the anti-PTPσ antibody may be immobilized on a surface and the cells collected by separating the surface from the sample. The method may include collecting $PTP\sigma^-$ cells that are $CD34^+$, $CD38^-$, $CD45RA^-$, $CD90^+$, $lin^-$, $Rho^{lo}$, $CD49f^{+-}$, and/or $CD33^-$ cells.

In some aspects, the invention relates to a method for preparing a sample of HSCs for implantation by contacting the sample with an inhibitor of the PTPσ pathway. In other aspects, the invention provides a method for implanting hematopoietic cells into a subject in need thereof, comprising obtaining a sample comprising hematopoietic cells, contacting the sample with an inhibitor of the PTPσ pathway, and transplanting the sample into the subject. In some embodiments of these methods, the PTPσ pathway inhibitor may be a PTPσ inhibitor, p250GAP antagonist, or a Rac1 agonist. The inhibitor of the PTPσ pathway may be a small molecule, an antibody, or an interfering nucleic acid, such as an siRNA (e.g., a shRNA). In some embodiments, the method comprises removing such cells as $PTP\sigma^+$, CD34–, $CD38^+$, $CD45RA^+$, $CD90^-$, $lin^+$, $Rho^{hi}$, $CD49f^-$, and/or $CD33^+$ cells from the sample. In some embodiments, the method includes enriching the hematopoietic cells in certain cell types, for example, in $PTP\sigma^-$, $CD34^+$, $CD38^-$, $CD45RA^-$, $CD90^+$, $lin^-$, $Rho^{lo}$, $CD49f^{+-}$, and/or $CD33^-$ cells from the sample.

In some aspects, the invention relates to a method for increasing a population of $PTP\sigma^-$ hematopoietic cells in a subject in need thereof, by administering to the subject an effective amount of an inhibitor of a PTPσ pathway. In other aspects, the invention relates to a method for promoting hematopoietic reconstitution in a subject in need thereof, by administering to the subject an inhibitor of a PTPσ pathway. In some embodiments of these methods, the subject has received an implant comprising hematopoietic cells, e.g., a cord blood implant or a bone marrow implant. In some embodiments, the method further comprises administering hematopoietic cells to the patient, for example, before the subject receives the implant, simultaneously with the implant, and/or after the subject receives the implant. In some embodiments, the subject has compromised hematopoietic function. The inhibitor of the PTPσ pathway may be a PTPσ inhibitor, a p250GAP antagonist, or a Rac1 agonist. The inhibitor of the PTPσ pathway may be a small molecule, an antibody, or an interfering nucleic acid, such as a siRNA (e.g., a shRNA). In some embodiments, the inhibitor is administered systemically. The inhibitor may accelerate hematologic recovery, e.g., to counter the effects of myelosuppressive therapy (e.g., chemotherapy and/or radiation therapy). The PTPσ pathway inhibitor can be administered prior, concurrently, or after the chemotherapy and/or radiation therapy. In some embodiments of these methods, the subject has been exposed to radiation. Exemplary subjects include mammals (e.g., a mouse or, preferably, a human).

DETAILED DESCRIPTION OF THE DISCLOSURE

Figure 1A:
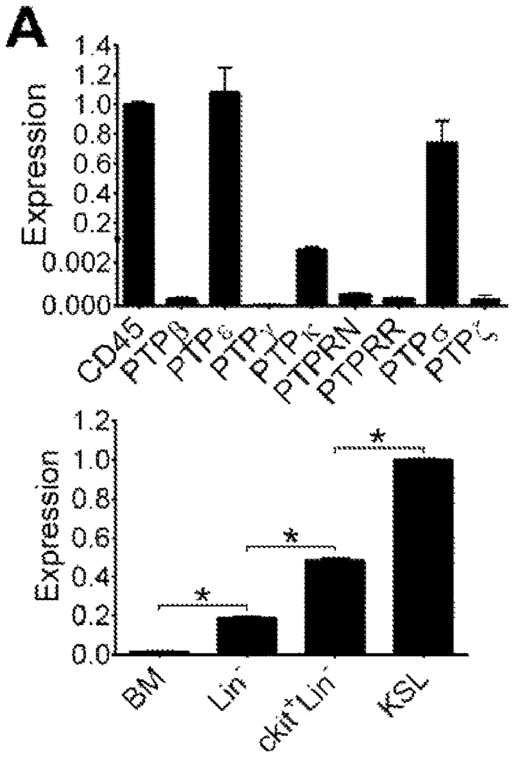
FIG. 1. Deletion of PTPσ augments HSC repopulating capacity. (1A) Mean expression of receptor PTPs in BM KSL cells by qRTPCR is shown (top) and expression of PTPσ within hematopoietic cell subsets (bottom, $Lin^-$=lineage negative; n=3-9/group). (1B) Mean (±SEM) numbers of CFCs are shown from 12 week $PTP\sigma^{-/-}$ and $PTP\sigma^{+/+}$ mice. *P=0.002 (n=6, Mann-Whitney). (1C) Mean levels of donor $CD45.2^+$ hematopoietic cell engraftment are shown in the PB of $CD45.1^+$ mice at 16 weeks following competitive transplantation of $3\times10^4$ BM cells from $PTP\sigma^{+/+}$ or $PTP\sigma^{-/-}$ mice. *P<0.0001 (n=15-18/group, Mann-Whitney). Multilineage engraftment of Mac-1/Gr-$1^+$, $B220^+$ and $CD3^+$ donor cells is shown at right. *P=0.008, P=0.0001, P=0.04, respectively (Mann-Whitney). (1D) Multilineage flow cytometric analysis of donor hematopoietic cell engraftment in the PB is shown from mice competitively transplanted with BM cells from $PTP\sigma^{+/+}$ or $PTP\sigma^{-/-}$ mice at 16 weeks post-transplant. Quadrant numbers represent the percentages of donor lineage cells. (1E) In the top panel, mean donor $CD45.2^+$ cell engraftment in the PB is shown over time following transplantation of BM cells from $PTP\sigma^{+/+}$ or $PTP\sigma^{-/-}$ mice in primary recipient mice. *P<0.0001, P=0.0001, P=0.001, and P<0.0001 for engraftment at 4, 8, 12 and 16 weeks, respectively. At bottom, mean donor $CD45.2^+$ cell engraftment in secondary transplanted mice is shown over time. *P=0.004, P=0.01, P=0.005, and P=0.002 for engraftment at 4, 8, 12 and 16 weeks, respectively (n=7-8/group, Mann-Whitney). PTP abbreviations: β=beta, ε-epsilon, γ=gamma, κ=kappa, N=receptor type N, R=receptor type R, ζ-zeta.

Some aspects of the invention are based on the finding that receptor protein tyrosine phosphatase-sigma (PTPσ) is significantly overexpressed in mouse and human HSCs compared to more mature hematopoietic cells. Further, bone marrow (BM) cells from $PTP\sigma^{-/-}$ mice display a markedly increased competitive repopulating capacity compared to $PTP\sigma^{+/+}$ BM cells. In some aspects, the invention relates to the finding that the increased functional capacity of $PTP\sigma^{-/-}$ HSCs was associated with increased activation of the RhoGTPase, Rac1. For example, inhibition of Rac1 blocks the augmented migration capacity of $PTP\sigma^{-/-}$ cells. Additionally, some aspects of the invention relate to the finding that the negative selection of human cord blood (CB) HSCs for PTPσ led to a 15-fold increase in repopulating capacity as compared to human $PTP\sigma^+$ HSCs.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The terms "agonist", "antagonist", and "inhibitor" are used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal cells or tissues. They include, for example, agents whose structure is known, and those whose structure is not known. An agonist refers to an agent that increases the activity of a protein. For example, a Rac1 agonist may increase the amount of Rac1-GTP in a cell. The terms "antagonist" and "inhibitor" are used interchangeably herein. An inhibitor may, for example, reduce the phosphatase activity of PTPσ. The inhibitor may inhibit a target such as PTPσ by reducing the amount of translation of a PTPσ mRNA, e.g., the inhibitor may be an interfering nucleic acid. Similarly, an inhibitor may reduce the phosphatase activity of PTPσ by, for example, binding to a conformation of PTPσ that has reduced phosphatase activity.

The term "agent" is used to refer to an "agonist", "antagonist", or "inhibitor", and the term includes small molecules, interfering nucleic acids, and viral vectors. The term "agent" is used interchangeably with the term "compound" herein.

The terms "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition to an asymptomatic subject which reduces the frequency or severity of, or delays the onset of, symptoms of a medical condition in the subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapies such that the second therapy is administered while the previously administered therapy is still effective in the body (e.g., the two compounds are simultaneously effective in the patient, which may include synergistic effects of the two compounds). For example, the different therapies can be administered either in the same formulation or in a separate formulations, either concomitantly or sequentially. In certain embodiments, the different therapies can be administered within one hour, 12 hours, 24 hours, 36 hours, 48 hours, 72 hours, or a week of one another. Thus, an individual who receives such treatment can benefit from a combined effect of different therapies.

A "therapeutically effective amount" ("effective amount") or a "therapeutically effective dose" of a therapy or agent, such as an agonist, antagonist, or inhibitor, is an amount of a drug or therapy that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated. The skilled worker can readily determine the effective amount for a given situation by routine experimentation.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono- or di-acid salts can be formed, and such salts may exist in either a hydrated, solvated or substantially anhydrous form. The selection of the appropriate salt will be known to one skilled in the art.

The term "pharmaceutically acceptable basic addition salt" as used herein means any non-toxic organic or inorganic base addition salt of any acid compounds. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

Populations of Cells

In some aspects, the invention relates to a population of mammalian cells comprising hematopoietic stem cells ("HSCs"), wherein the population is substantially free of cells that express protein tyrosine phosphatase sigma ("PTPσ"). The population may further comprise an inhibitor of the PTPσ pathway.

The term "substantially free of cells that express", such as in a "population of cells that is substantially free of cells that express PTPσ", may refer to compositions in which cells that express a high level of the molecule have been substantially removed and cells that express a low level of the molecule remain. The skilled artisan will recognize that a population of cells that is substantially free of cells that express PTPσ may comprise cells that express a detectable amount of PTPσ. Further, the skilled artisan will recognize that the threshold for distinguishing cells that express a high level of a molecule from cells that express a low level of a molecule may vary according to the overall context in which the distinction is being made. When two discrete populations of cell cannot be identified, the term "substantially free of cells that express [a molecule]" refers to the selection of cells that express low levels of the molecule. For example, FIG. 5B shows various flow cytometry gates that do not distinguish two discrete populations of cells. In this case, the term substantially free of cells that express PTPσ refers to cells that are gated as low-expressing cells. A population of cells that is substantially free of cells that express PTPσ may therefore be obtained, for example, by collecting the gated cells. The placement of the gate may be arbitrary. Thus, the population of cells that is substantially free of cells that express PTPσ may be generated, for example, by gating a population of cells that comprises less than 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, or 25% of the cells in a sample, wherein the gated cells were determined to express the least amount PTPσ. Similarly, the population of cells that is substantially free of cells that express PTPσ may be generated, for example, by removing at least 10%, 15%, 20%, 25%, 30%, 35%, 40%, 45%, 50%, 55%, 60%, 65%, or 70% of the cells that express the most PTPσ from the sample. Those with skill in the art will know that the gate may be adjusted based on other gates, for example, based on gates that select for other characteristics of HSCs.

In some embodiments, the invention relates to a population of mammalian cells comprising HSCs, wherein the population is enriched in $PTPσ^-$ cells. The population may further comprise an inhibitor of the PTPσ pathway.

The term "enriched" refers to a population that has been processed to either collect cells that possess the enriched characteristic or to remove cells that do not possess the characteristic. The skilled artisan will recognize that a characteristic such as $PTPσ^-$ or $PTPσ^+$ may be arbitrarily defined. As described herein, $PTPσ^+$ cells express more PTPσ on average than $PTPσ^-$ cells, such as during the sorting of a population of cells. A population is enriched in $PTPσ^-$ cells if the population is obtained by preferentially collecting cells that express low levels of PTPσ relative to cells that express higher levels of PTPσ, for example by FACS or MACS. Similarly, a population is enriched in $PTPσ^-$ cells if the population is obtained by preferentially removing cells that express high levels of PTPσ relative to cells that express lower levels of PTPσ.

In some aspects, the invention relates to a population of mammalian cells comprising HSCs and an inhibitor of the PTPσ pathway.

In some embodiments, the invention relates to a cell population, wherein the population is enriched in $CD34^+$, $CD38^-$, $CD45RA^-$, $CD90^+$, $lin^-$, $Rho^{lo}$, $CD49f^{+-}$, and/or $CD33^-$ cells. The population may be enriched, for example, in $CD34^+CD38^-CD45RA^-Lin^-$ cells or $CD34^+CD38^-CD45RA^-Lin^-PTPσ^-$ cells. Similarly, in some embodiments, the invention relates to a cell population, wherein the population is substantially free of $CD34^-$, $CD38^+$, $CD45RA^+$, $CD90^-$, $lin^+$, $Rho^{hi}$, $CD49f^-$, and/or $CD33^+$ cells. The HSCs of the invention may be, for example, mice or human HSCs. In some embodiments, the HSCs are cord blood or bone marrow HSCs.

Inhibitors of the PTPσ Pathway

In some aspects, the invention relates to an inhibitor of the PTPσ pathway. The inhibitor may be an interfering nucleic acid, such as an shRNA, a small molecule, or an antibody. The inhibitor of the PTPσ pathway may be a PTPσ inhibitor, a p250GAP antagonist, or a Rac1 agonist.

Interfering Nucleic Acids

In certain embodiments, interfering nucleic acid molecules that selectively target PTPσ and downstream signaling proteins such as p250GAP are provided herein and/or used in methods described herein. Interfering nucleic acids generally include a sequence of cyclic subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid:oligomer heteroduplex within the target sequence. Interfering RNA molecules include, but are not limited to, antisense molecules, siRNA molecules, single-stranded siRNA molecules, miRNA molecules and shRNA molecules. Typically, at least 17, 18, 19, 20, 21, 22 or 23 nucleotides of the complement of the target mRNA sequence are sufficient to mediate inhibition of a target transcript. Perfect complementarity is not necessary. In some embodiments, the interfering nucleic acid molecule is double-stranded RNA. The double-stranded RNA molecule may have a 2 nucleotide 3' overhang. In some embodiments, the two RNA strands are connected via a hairpin structure, forming a shRNA molecule. shRNA molecules can contain hairpins derived from microRNA molecules. For example, an RNAi vector can be constructed by cloning the interfering RNA sequence into a pCAG-miR30 construct containing the hairpin from the miR30 miRNA. RNA interference molecules may include DNA residues, as well as RNA residues. Interfering nucleic acids that target PTPσ include those described in the examples.

Interfering nucleic acid molecules provided herein can contain RNA bases, non-RNA bases or a mixture of RNA bases and non-RNA bases. For example, interfering nucleic acid molecules provided herein can be primarily composed of RNA bases but also contain DNA bases or non-naturally occurring nucleotides.

The interfering nucleic acids can employ a variety of oligonucleotide chemistries. Examples of oligonucleotide chemistries include, without limitation, peptide nucleic acid (PNA), linked nucleic acid (LNA), phosphorothioate, 2'O-Me-modified oligonucleotides, and morpholino chemistries, including combinations of any of the foregoing. In general, PNA and LNA chemistries can utilize shorter targeting sequences because of their relatively high target binding strength relative to 2'O-Me oligonucleotides. Phosphorothioate and 2'O-Me-modified chemistries are often combined to generate 2'O-Me-modified oligonucleotides having a phosphorothioate backbone (See, e.g., PCT Publication Nos. WO/2013/112053; U.S. Pat. No. 8,609,065, incorporated by reference).

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm, Buchardt et al., Nature, 365:566-68 (1993)). The backbone of PNAs is formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases. One type of PNA is an antisense oligonucleotide (ASO), in which 15 to 20 chemically modified deoxynucleotides or ribonucleotides form a polymer that has sequence complimentarily to a mRNA sequence of interest. Despite a radical structural change to the natural structure, PNAs are capable of sequence-specific binding in a helix form to DNA or RNA. Characteristics of PNAs include a high binding affinity to complementary DNA or RNA, a destabilizing effect caused by single-base mismatch, resistance to nucleases and proteases, hybridization with DNA or RNA independent of salt concentration and triplex formation with homopurine DNA. Panagene has developed proprietary benzothiazole-2-sulfonyl-PNA monomers (Bts PNA) and proprietary oligomerization processes. The PNA oligomerization using Bts PNA monomers is composed of repetitive cycles of deprotection, coupling and capping. PNAs can be produced synthetically using any technique known in the art (See, e.g., U.S. Pat. Nos. 6,969,766, 7,211,668, 7,022,851, 7,125,994, 7,145,006 and 7,179,896, which are incorporated by reference. See also U.S. Pat. Nos. 5,539,082; 5,714,331; and 5,719,262 for the preparation of PNAs, which are incorporated by reference). Further teaching of PNA compounds can be found in Nielsen et al., Science, 254:1497-1500 (1991).

Interfering nucleic acids may also contain "locked nucleic acid" subunits (LNAs). "LNAs" are a member of a class of modifications called bridged nucleic acid (BNA). BNA is characterized by a covalent linkage that locks the conformation of the ribose ring in a C30-endo (northern) sugar pucker. For LNA, the bridge is composed of a methylene between the 2'-O and the 4'-C positions. LNA enhances backbone preorganization and base stacking to increase hybridization and thermal stability.

The structures of LNAs can be found, for example, in Chemical Communications, 455-56 (1998); Tetrahedron, 54:3607 (1998); Accounts Chemical Research, 32:301 (1999); Tetrahedron Letters, 38:8735-38 (1997); Tetrahedron Letters, 39:5401-04 (1998); and Bioorganic Medicinal Chemistry, 16:9230-37 (2008).

Compounds provided herein may incorporate one or more LNAs; in some cases, the compounds may be entirely composed of LNAs. Methods for the synthesis of individual LNA nucleoside subunits and their incorporation into oligonucleotides are described, for example, in U.S. Pat. Nos. 7,572,582, 7,569,575, 7,084,125, 7,060,809, 7,053,207, 7,034,133, 6,794,499, and 6,670,461, each of which is incorporated by reference. Typical intersubunit linkers include phosphodiester and phosphorothioate moieties; alternatively, non-phosphorous containing linkers may be employed. One embodiment is an LNA containing compound where each LNA subunit is separated by a DNA subunit. Certain compounds are composed of alternating LNA and DNA subunits where the intersubunit linker is phosphorothioate.

"Phosphorothioates" (or S-oligos) are a variant of normal DNA in which one of the nonbridging oxygens is replaced by a sulfur. The sulfurization of the internucleotide bond reduces the action of endo- and exonucleases including 5' to 3' and 3' to 5' DNA POL 1 exonuclease, nucleases Si and Pi, RNases, serum nucleases and snake venom phosphodiesterase. Phosphorothioates are made by two principal routes: by the action of a solution of elemental sulfur in carbon disulfide on a hydrogen phosphonate, or by the method of sulfurizing phosphite triesters with either tetraethylthiuram disulfide (TETD) or 3H-1,2-bensodithiol-3-one 1,1-dioxide (BDTD) (See, e.g., Iyer et al., J. Organic Chemistry 55:4693-4699 (1990)). The latter methods avoid the problem of elemental sulfur's insolubility in most organic solvents and the toxicity of carbon disulfide. The TETD and BDTD methods also yield higher purity phosphorothioates.

"2'O-Me oligonucleotides" molecules carry a methyl group at the 2'-OH residue of the ribose molecule. 2'-O-Me-RNAs show the same (or similar) behavior as DNA, but are protected against nuclease degradation. 2'-O-Me-RNAs can also be combined with phosphorothioate oligonucleotides (PTOs) for further stabilization. 2'O-Me oligonucleotides (phosphodiester or phosphorothioate) can be synthesized according to routine techniques in the art (See, e.g., Yoo et al., Nucleic Acids Research 32:2008-16 (2004)).

The interfering nucleic acids described herein may be contacted with a cell or administered to an organism (e.g., a human). Alternatively, constructs and/or vectors encoding the interfering RNA molecules may be contacted with or introduced into a cell or organism. In certain embodiments, a viral vector is used. The viral vector may be an adenovirus vector; an adeno-associated virus vector; a pox virus vector, such as a fowlpox virus vector; an alpha virus vector; a baculoviral vector; a herpes virus vector; a retrovirus vector, such as a lentivirus vector; a Modified Vaccinia virus Ankara vector; a Ross River virus vector; a Sindbis virus vector; a Semliki Forest virus vector; and a Venezuelan Equine Encephalitis virus vector. In some embodiments, the vector has a tropism for hematopoietic cells. In some embodiments the vector is a lentiviral vector.

Typically at least 17, 18, 19, 20, 21, 22 or 23 nucleotides of the complement of the target mRNA sequence are sufficient to mediate inhibition of a target transcript. Perfect complementarity is not necessary. In some embodiments, the interfering nucleic acids contain a 1, 2 or 3 nucleotide mismatch with the target sequence. The interfering nucleic acid molecule may have a 2 nucleotide 3' overhang. If the interfering nucleic acid molecule is expressed in a cell from a construct, for example from a hairpin molecule or from an inverted repeat of the desired sequence, then the endogenous cellular machinery will create the overhangs. shRNA molecules can contain hairpins derived from microRNA molecules. For example, an RNAi vector can be constructed by cloning the interfering RNA sequence into a pCAG-miR30 construct containing the hairpin from the miR30 miRNA. RNA interference molecules may include DNA residues, as well as RNA residues.

In some embodiments, the interfering nucleic acid molecule is a siRNA molecule. Such siRNA molecules should include a region of sufficient homology to the target region, and be of sufficient length in terms of nucleotides, such that the siRNA molecule down-regulate target RNA. The term "ribonucleotide" or "nucleotide" can, in the case of a modified RNA or nucleotide surrogate, also refer to a modified nucleotide, or surrogate replacement moiety at one or more positions. It is not necessary that there be perfect complementarity between the siRNA molecule and the target, but the correspondence must be sufficient to enable the siRNA molecule to direct sequence-specific silencing, such as by RNAi cleavage of the target RNA. In some embodiments, the sense strand need only be sufficiently complementary with the antisense strand to maintain the overall double-strand character of the molecule.

In addition, an siRNA molecule may be modified or include nucleoside surrogates. Single stranded regions of an siRNA molecule may be modified or include nucleoside surrogates, e.g., the unpaired region or regions of a hairpin structure, e.g., a region which links two complementary regions, can have modifications or nucleoside surrogates. Modification to stabilize one or more 3'- or 5'-terminus of an siRNA molecule, e.g., against exonucleases, or to favor the antisense siRNA agent to enter into RISC are also useful. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis.

Each strand of an siRNA molecule can be equal to or less than 35, 30, 25, 24, 23, 22, 21, or 20 nucleotides in length. In some embodiments, the strand is at least 19 nucleotides in length. For example, each strand can be between 21 and 25 nucleotides in length. In some embodiments, siRNA agents have a duplex region of 17, 18, 19, 29, 21, 22, 23, 24, or 25 nucleotide pairs, and one or more overhangs, such as one or two 3' overhangs, of 2-3 nucleotides.

A "small hairpin RNA" or "short hairpin RNA" or "shRNA" includes a short RNA sequence that makes a tight hairpin turn that can be used to silence gene expression via RNA interference. The shRNAs provided herein may be chemically synthesized or transcribed from a transcriptional cassette in a DNA plasmid. The shRNA hairpin structure is cleaved by the cellular machinery into siRNA, which is then bound to the RNA-induced silencing complex (RISC).

In some embodiments, shRNAs are about 15-60, 15-50, or 15-40 (duplex) nucleotides in length, about 15-30, 15-25, or 19-25 (duplex) nucleotides in length, or are about 20-24, 21-22, or 21-23 (duplex) nucleotides in length (e.g., each complementary sequence of the double-stranded shRNA is 15-60, 15-50, 15-40, 15-30, 15-25, or 19-25 nucleotides in length, or about 20-24, 21-22, or 21-23 nucleotides in length, and the double-stranded shRNA is about 15-60, 15-50, 15-40, 15-30, 15-25, or 19-25 base pairs in length, or about 18-22, 19-20, or 19-21 base pairs in length). shRNA duplexes may comprise 3' overhangs of about 1 to about 4 nucleotides or about 2 to about 3 nucleotides on the antisense strand and/or 5'-phosphate termini on the sense strand. In some embodiments, the shRNA comprises a sense strand and/or antisense strand sequence of from about 15 to about 60 nucleotides in length (e.g., about 15-60, 15-55, 15-50, 15-45, 15-40, 15-35, 15-30, or 15-25 nucleotides in length), or from about 19 to about 40 nucleotides in length (e.g., about 19-40, 19-35, 19-30, or 19-25 nucleotides in length), or from about 19 to about 23 nucleotides in length (e.g., 19, 20, 21, 22, or 23 nucleotides in length).

Non-limiting examples of shRNA include a double-stranded polynucleotide molecule assembled from a single-stranded molecule, where the sense and antisense regions are linked by a nucleic acid-based or non-nucleic acid-based linker; and a double-stranded polynucleotide molecule with a hairpin secondary structure having self-complementary sense and antisense regions. In some embodiments, the sense and antisense strands of the shRNA are linked by a loop structure comprising from about 1 to about 25 nucleotides, from about 2 to about 20 nucleotides, from about 4 to about 15 nucleotides, from about 5 to about 12 nucleotides, or 1, 2, 3, 4, 5, 6, 7, 8, 9, 10, 11, 12, 13, 14, 15, 16, 17, 18, 19, 20, 21, 22, 23, 24, 25, or more nucleotides.

Additional embodiments related to the shRNAs, as well as methods of designing and synthesizing such shRNAs, are described in U.S. patent application publication number 2011/0071208, which is herein incorporated by reference.

Suitable methods for making shRNAs are described in the examples, and those with ordinary skill in the art will recognize that many other nucleotide sequences may be designed to inhibit the PTPσ pathway.

In some embodiments, provided herein are micro RNAs (miRNAs). miRNAs represent a large group of small RNAs produced naturally in organisms, some of which regulate the expression of target genes. miRNAs are formed from an approximately 70 nucleotide single-stranded hairpin precursor transcript by Dicer. miRNAs are not translated into proteins, but instead bind to specific messenger RNAs, thereby blocking translation. In some instances, miRNAs base-pair imprecisely with their targets to inhibit translation.

In some embodiments, antisense oligonucleotide compounds are provided herein. In certain embodiments, the degree of complementarity between the target sequence and antisense targeting sequence is sufficient to form a stable duplex. The region of complementarity of the antisense oligonucleotides with the target RNA sequence may be as short as 8-11 bases, but can be 12-15 bases or more, e.g., 10-40 bases, 12-30 bases, 12-25 bases, 15-25 bases, 12-20 bases, or 15-20 bases, including all integers in between these ranges. An antisense oligonucleotide of about 14-15 bases is generally long enough to have a unique complementary sequence.

In certain embodiments, antisense oligonucleotides may be 100% complementary to the target sequence, or may include mismatches, e.g., to improve selective targeting of allele containing the disease-associated mutation, as long as a heteroduplex formed between the oligonucleotide and target sequence is sufficiently stable to withstand the action of cellular nucleases and other modes of degradation which may occur in vivo. Hence, certain oligonucleotides may have about or at least about 70% sequence complementarity, e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence complementarity, between the oligonucleotide and the target sequence. Oligonucleotide backbones that are less susceptible to cleavage by nucleases are discussed herein. Mismatches, if present, are typically less destabilizing toward the end regions of the hybrid duplex than in the middle. The number of mismatches allowed will depend on the length of the oligonucleotide, the percentage of G:C base pairs in the duplex, and the position of the mismatch(es) in the duplex, according to well understood principles of duplex stability.

Interfering nucleic acid molecules can be prepared, for example, by chemical synthesis, in vitro transcription, or digestion of long dsRNA by Rnase III or Dicer. These can be introduced into cells by transfection, electroporation, or other methods known in the art (See Hannon, Nature, 418:244-51 (2002); Bernstein et al., RNA, 7:1509-21 (2002); Hutvagner et al., Current Opinion Genetics & Development, 12:225-32 (2002); Brummelkamp, Science, 296:550-53 (2002); Lee et al., Nature Biotechnology, 20:500-05 (2002); Miyagishi & Taira, Nature Biotechnology, 20:497-00 (2002); Paddison et al., Genes & Development, 16:948-58 (2002); Paul et al., Nature Biotechnology, 20:505-08 (2002); Sui et al., Proceedings Nat'l Academy Sci. USA, 99:5515-20 (2002); Yu et al., Proceedings Nat'l Academy Sci. USA, 99:6047-52 (2002)).

In the present methods, an interfering nucleic acid molecule or an interfering nucleic acid encoding polynucleotide can be administered to the subject, for example, as naked nucleic acid, in combination with a delivery reagent, and/or as a nucleic acid comprising sequences that express an interfering nucleic acid molecule. In some embodiments the nucleic acid comprising sequences that express the interfering nucleic acid molecules are delivered within vectors, e.g. plasmid, viral and bacterial vectors. Any nucleic acid delivery method known in the art can be used in the methods described herein. Suitable delivery reagents include, but are not limited to, e.g., the Mirus Transit TKO lipophilic reagent; lipofectin; lipofectamine; cellfectin; polycations (e.g., polylysine), atelocollagen, nanoplexes and liposomes. The use of atelocollagen as a delivery vehicle for nucleic acid molecules is described in Minakuchi et al. Nucleic Acids Research, 32:e109 (2004); Hanai et al. Annals N.Y. Acad. Sci., 1082:9-17 (2006); Kawata et al. Molecular Cancer Therapeutics, 7:2904-12 (2008). Exemplary interfering nucleic acid delivery systems are provided in U.S. Pat. Nos. 8,283,461, 8,313,772, 8,501,930. 8,426,554, 8,268,798 and 8,324,366, each of which is hereby incorporated by reference.

Antibodies

The term "antibody" herein is used in the broadest sense and specifically covers monoclonal antibodies, polyclonal antibodies, multispecific antibodies (e.g., bispecific antibodies) formed from at least two intact antibodies, and antibody fragments so long as they exhibit the desired biological activity, e.g., inhibition of a PTPσ pathway.

The basic 4-chain antibody unit is a heterotetrameric glycoprotein composed of two identical light (L) chains and two identical heavy (H) chains. The pairing of a $V_H$ and $V_L$ together forms a single antigen-binding site. For the structure and properties of the different classes of antibodies, see, e.g., Basic and Clinical Immunology, 8th Ed., Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ") and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three dimensional configurations of different classes of immunoglobulins are well known and described generally in, for example, Abbas et al., Cellular and Molecular Immunology, $4^{th}$ ed. (W.B. Saunders Co., 2000).

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_R$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

An "isolated' antibody is one that has been identified, separated and/or recovered from a component of its production environment (e.g., naturally or recombinantly). Preferably, the isolated polypeptide is free of association with all other contaminant components from its production environment.

Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T-cells since at least one component of the antibody's natural environment will not be present. Ordinarily, however, an isolated polypeptide or antibody will be prepared by at least one purification step.

The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies, such as the antibodies described herein. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., Sequences of Immunological Interest, Fifth Edition, National Institute of Health, Bethesda, Md. (1991)). The constant domains are not involved directly in the binding of antibody to an antigen, but exhibit various effector functions, such as participation of the antibody in antibody-dependent-cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, Nature, 256:495-97 (1975); Hongo et al., Hybridoma, 14 (3):253-260 (1995), Harlow et al., Antibodies: A Laboratory Manual, (Cold Spring Harbor Laboratory Press, 2d ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352:624-628 (1991); Marks et al., J. Mol. Biol. 222:581-597 (1992); Sidhu et al., J. Mol. Biol. 338(2): 299-310 (2004); Lee et al., J. Mol. Biol. 340(5): 1073-1093 (2004); Fellouse, Proc. Nat'l Acad. Sci. USA 101(34): 12467-472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Nat'l Acad. Sci. USA 90:2551 (1993); Jakobovits et al., Nature 362:255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al., Bio/Technology 10:779-783 (1992); Lonberg et al., Nature 368:856-859 (1994); Morrison, Nature 368:812-813 (1994); Fishwild et al., Nature Biotechnol. 14:845-851 (1996); Neuberger, Nature Biotechnol. 14:826 (1996); and Lonberg and Huszar, Intern. Rev. Immunol. 13:65-93 (1995).

The terms "full-length antibody," "intact antibody" or "whole antibody" are used interchangeably to refer to an antibody in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', $F(ab')_2$ and Fv fragments; diabodies; linear antibodies (see U.S. Pat. No. 5,641,870, Example 2; Zapata et al., Protein Eng. 8(10): 1057-1062 (1995)); single-chain antibody molecules and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_R$I). Each Fab fragment is monovalent with respect to antigen binding, i.e., it has a single antigen-binding site. Pepsin treatment of an antibody yields a single large $F(ab')_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H$I domain including one or more cysteines from the antibody hinge region. Fab'-SH is the designation herein for Fab' in which the cysteine residue(s) of the constant domains bear a free thiol group. $F(ab)_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pliickthun in The Pharmacology of Monoclonal Antibodies, vol. 113, Rosenburg and Moore eds., Springer-Verlag, New York, pp. 269-315 (1994).

"Functional fragments" of antibodies comprise a portion of an intact antibody, generally including the antigen binding or variable region of the intact antibody or the F region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites.

Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., Proc. Nat'l Acad. Set USA 90:6444-48 (1993).

As used herein, a "chimeric antibody" refers to an antibody (immunoglobulin) of the present disclosure, in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Nat'l Acad. Sci. USA, 81:6851-55 (1984)). Chimeric antibodies of interest herein include PREVIATIZED® antibodies wherein the antigen-binding region of the antibody is derived from an antibody produced by, e.g., immunizing macaque monkeys with an antigen of interest. As used herein, "humanized antibody" is a subset of "chimeric antibodies."

"Humanized' forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR of the recipient are replaced by residues from an HVR of a non-human species (donor antibody) such as mouse, rat, rabbit or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, and the like. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, for example, Vaswani and Hamilton, Ann. Allergy, Asthma & Immunol. 1: 105-115 (1998); Harris, Biochem. Soc. Transactions 23: 1035-1038 (1995); Hurle and Gross, Curr. Op. Biotech. 5:428-433 (1994); and U.S. Pat. Nos. 6,982,321 and 7,087,409.

A "human antibody" is one that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, Mol. Biol., 227:381 (1991); Marks et al., Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol. 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Nat'l Acad. Sci. USA, 103:3557-3562 (2006) regarding human antibodies generated via a human B-cell hybridoma technology.

Antibodies that selectively or broadly target PTPσ or downstream signaling proteins are useful in the compositions and methods described herein, e.g., as inhibitors of the PTPσ pathway. For example, in certain embodiments, the compositions and methods described herein employ an antibody that inhibits or blocks the PTPσ pathway. The antibody refers to antibodies including antibodies of different isotypes, such as IgM, IgG, IgA, IgD, and IgE antibodies. The antibody may be a polyclonal antibody, a monoclonal antibody, a chimerized or chimeric antibody, a humanized antibody, a primatized antibody, a deimmunized antibody, or a fully human antibody. The antibody can be made in or of any variety of species, e.g., mammals such as humans, non-human primates (e.g., orangutan, baboons, or chimpanzees), horses, cattle, pigs, sheep, goats, dogs, cats, rabbits, guinea pigs, gerbils, hamsters, rats, and mice. The antibody can be a purified and/or a recombinant antibody. The antibody may be a bispecific or multispecific antibody, or antigen-binding fragment thereof, for PTPσ protein. The antibody may target PTPσ protein, or the antibody may target PTPσ's downstream effectors. The antibody, or antigen-binding fragment thereof, may be murine, chimeric, humanized, composite, or human. The antibody may be detectably labeled.

Small Molecules

In certain embodiments, small molecules may be utilized to target PTPσ and downstream signaling proteins, e.g., as inhibitors of the PTPσ pathway. Small molecules which inhibit the PTPσ pathway or modulate the biological activity of PTP a are known in the art and described below as formulas I through IV as well as in U.S. Patent Application Publication No. 2012/0045459, herein incorporated by reference).

For example, suitable sulfonamides include compounds of the formula:

$$R_1—NH—SO_2—R_2—O—(CH_2)_n—CO—NR_3R_4 \quad (I)$$

where n is 1 thru 3;

where $R_1$ is:

$C_1$-$C_4$ alkyl;

$C_3$-$C_7$ cycloalkyl;

phenyl-$(CH_2)_m$— where m is 0 thru 2 and phenyl is optionally substituted with one or two $CH_3$—, $C_2H_5$—, F— and Cl—;

phenyl-$CH(CH_3)$— where phenyl is optionally substituted with $CH_3$—, $C_2H_5$—, F— and Cl—;

where $R_2$ is phenyl optionally substituted with one F—, Cl—, $CH_3$—, $C_2H_5$—, and $(CH_3)_2CH$—;

where $R_3$ is H—:

where $R_4$ is:

$C_1$-$C_3$ alkyl;

$C_3$-$C_7$ cycloalkyl;

—$CH_2$—CH═$CH_2$;

—$(CH_2)_z$—O—$R_5$ where z is 1 thru 5 and $R_5$ is $C_1$-$C_3$alkyl;

—$(CH_2)_w$—R where w is 1 thru 3 and $R_6$ is tetrahydrofuran or $C_3$-$C_7$ cycloalkyl optionally containing one double bond;

—$(CH_2)_w$—$R_7$ where $R_7$ is $C_1$-$C_3$ alkyl and $C_1$-$C_2$ alkoxy and where w is as defined above;

where $R_3$ and $R_4$ are taken together with the attached nitrogen atom to form a piperidinyl, piperazinyl, morpholinyl, pyrrolidinyl and pyridinyl ring;

and pharmaceutically acceptable salts thereof.

Similarly, suitable inhibitors include compounds having a structure of the formula:

(II)

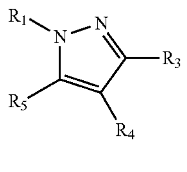

where $R_1$ is H—, $CH_3$—, $C_2H_5$— and cyclo $C_3H_5$—;

where $R_3$ is H—, F—, Cl—, Br—, I—, —$NO_2$, $R_{3-1}$-phenyl-CO—NH— where $R_{3-1}$ is $CH_3$—CO—, $CH_3$—, $C_2H_5$—, F—, Cl— and —$NO_2$;

where $R_4$ is H—, F—, Cl—, Br—, I—, —$NO_2$, —CO—$O^-$, $R_{4-1}$-phenyl-CO—NH— where $R_{4-1}$ is $CH_3$—CO—, $CH_3$—, $C_2H_5$—, F—, Cl— and —$NO_2$;

where $R_5$ is H—, F—, Cl—, Br—, I—, —$NO_2$, $R_{5-1}$-phenyl-CO—NH— where $R_{3-1}$ is $CH_3$—CO—, $CH_3$—, $C_2H_5$—, F—, Cl— and —$NO_2$;

optionally with the proviso:

(1) that one of $R_3$, $R_4$ and $R_5$ must be $R_{3-1}$-phenyl-CO—NH—, $R_{4-1}$-phenyl-CO—NH— or $R_{5-1}$-phenyl-CO—NH—;

and pharmaceutically acceptable salts thereof.

Other examples include ketoesters of the formula:

$$X_1—CO—O—CHR_1—CO—R_2 \quad (III)$$

where $X_1$ is fluoren-9-one;

where $R_1$ is:

H—, $C_1$-$C_3$ alkyl, phenyl optionally substituted with one or two

F—,

Cl,

—$NO_2$;

where $R_2$ is:

1-naphthyl, 2-naphthyl, phenyl optionally substituted with one or two $C_1$-$C_3$ alkyl, $C_1$-$C_2$ alkoxy,

F—,

Cl—,

Br—,

—$NO_2$,

—O—CO-phenyl optionally substituted with 1 F—, Cl— and $CH_3$—;

and pharmaceutically acceptable salts thereof.

Other suitable inhibitors have a structure of Formula IV:

(IV)

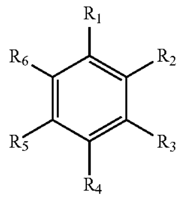

where $R_1$ is

—CO—$CH_3$

—CO—NH—$R_{1-1}$ where $R_{1-1}$ is naphthyl phenyl optionally substituted with one $CH_3$—CO—

$CH_3$—CO—NH— phenyl-CO—CH═CH—

Br—

Cl—

$^-$O—CO—;

where $R_2$ is —H, $C_1$-$C_2$ alkyl, —$(CH_2)_m$-phenyl where m is 1 or 2;

and where $R_2$ and $R_3$ are taken together with the atoms to which they are attached for form a phenyl ring optionally substituted with one —Cl, —Br and —$CH_3$;

where $R_3$ is —H, $C_1$-$C_2$ alkyl, —$NO_2$,
—CO—NH-phenyl-CO—$CH_3$,
—NH—CO—$R_{3-1}$ where $R_{3-1}$ is
phenyl optionally substituted with —O—CO—$CH_3$,
$C_1$-$C_3$ alkyl,
2-furanyl,
phthalimide,
coumarin,
—O—$CH_2$-phenyl optionally substituted with one Cl—, Br— and $CH_3$—,
—$SO_2$—$NR_{3-2}R_{3-3}$ where $R_{3-2}$ is
—H,
$C_1$-$C_3$ alkyl and where $R_{3-3}$ is
$C_1$-$C_3$ alkyl,
phenyl optionally substituted with one $C_1$-$C_2$ alkyl,
morpholinyl,
piperidinyl,
piperazinyl,
and where $R_3$ and $R_4$ are taken together with the atoms to which they are attached and —O—$CH_2$—O— to form a methylene dioxo ring;
where $R_4$ is H—, Cl—, Br— and $C_1$-$C_2$ alkyl;
and where $R_4$ and $R_3$ are taken together with the atoms to which they are attached and —O—$CH_2$—O— to form a methylene dioxo ring;
where $R_5$ is H—, $C_1$-$C_2$ alkyl, —NH—CO-phenyl, —NH—CO-phenyl-CO—$CH_3$ and —NH—CO—($C_1$-$C_2$ alkyl);
where $R_6$ is H— and Cl—.

Compositions and Modes of Administration

In some embodiments (such as the uses described above), the agents of the disclosure are formulated into pharmaceutical compositions for administration to subjects (such as human subjects) in a biologically compatible form suitable for administration in vivo. Accordingly, in another aspect, aspects disclosed herein provide a pharmaceutical composition comprising an agent of the disclosure in admixture with a suitable diluent or carrier. Such a composition is useful for treating the conditions described herein.

The compositions containing the agents of the disclosure can be prepared by known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The agents disclosed herein may be used in treating the conditions described herein, in the form of the free base, salts (preferably pharmaceutically acceptable salts), solvates, hydrates, prodrugs, isomers, or mixtures thereof. All forms are within the scope of the disclosure. Acid addition salts may be formed and provide a more convenient form for use; in practice, use of the salt form inherently amounts to use of the base form. The acids which can be used to prepare the acid addition salts include preferably those which produce, when combined with the free base, pharmaceutically acceptable salts, that is, salts whose anions are non-toxic to the subject organism in pharmaceutical doses of the salts, so that the beneficial properties inherent in the free base are not vitiated by side effects ascribable to the anions.

Pharmaceutically acceptable salts within the scope of the disclosure include those derived from the following acids; mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like.

Pharmaceutically acceptable carriers that may be used in compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose based substances, polyethylene glycol, sodium carboxymethylcellulose, polyacrylates, waxes, polyethylene polyoxypropylene block polymers, polyethylene glycol, and wool fat.

In accordance with the methods of the disclosure, the described agents may be administered to a patient in a variety of forms depending on the selected route of administration, as will be understood by those skilled in the art. The compositions of the disclosure may be administered orally or parenterally.

Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

In certain embodiments, pharmaceutical compositions suitable for parenteral administration may comprise the agents of the present disclosure in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

A composition comprising an agent of the present disclosure may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

In certain embodiments of the disclosure, compositions comprising an agent of the present disclosure can be administered orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and the like, each containing a predetermined amount of the agent of the present disclosure as an active ingredient.

In solid dosage forms for oral administration (capsules, tablets, pills, dragees, powders, granules, and the like), one or more compositions comprising the agent of the present disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the agents of the present disclosure, the liquid dosage forms may contain inert diluents commonly used in the art, such as water or other solvents, solubilizing agents and emulsifiers, such as ethyl alcohol (ethanol), isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active agents, salts and/or prodrugs thereof, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

A person skilled in the art would know how to prepare suitable formulations. Conventional procedures and ingredients for the selection and preparation of suitable formulations are described, for example, in Remington's Pharmaceutical Sciences (1990-18th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions.

The agents of the disclosure may be administered to a subject in need thereof alone or in combination with pharmaceutically acceptable carriers, as noted above, the proportion of which is determined by the solubility and chemical nature of the agent, chosen route of administration and standard pharmaceutical practice.

The dosage of the agents and/or compositions of the disclosure can vary depending on many factors such as the pharmacodynamic properties of the agent, the mode of administration, the age, health and weight of the recipient, the nature and extent of the symptoms, the frequency of the treatment and the type of concurrent treatment, if any, and the clearance rate of the agent in the subject to be treated. One of skill in the art can determine the appropriate dosage based on the above factors. The agents of the disclosure may be administered initially in a suitable dosage that may be adjusted as required, depending on the clinical response. To calculate the human equivalent dose (HED) from a dosage used in the treatment of age-dependent cognitive impairment in rats, the formula HED (mg/kg)=rat dose (mg/kg)×0.16 may be employed (see Estimating the Safe Starting Dose in Clinical Trials for Therapeutics in Adult Healthy Volunteers, December 2002, Center for Biologics Evaluation and Research). For example, using that formula, a dosage of 10 mg/kg in rats is equivalent to 1.6 mg/kg in humans. This conversion is based on a more general formula HED=animal dose in mg/kg×(animal weight in kg/human weight in kg)$^{0.33}$. Similarly, to calculate the HED from a dosage used in the treatment in mouse, the formula HED (mg/kg)=mouse dose (mg/kg)×0.08 may be employed (see Estimating the Safe Starting Dose in Clinical Trials for Therapeutics in Adult Healthy Volunteers, December 2002, Center for Biologics Evaluation and Research).

Methods Related to Cell Populations

In some embodiments, the invention relates to a method for enriching the hematopoietic stem cells in a sample, the method comprising: obtaining a sample comprising hematopoietic stem cells; and removing PTPσ$^+$ cells from the sample.

In some embodiments, the invention relates to a method for implanting an effective amount of hematopoietic cells into a subject in need thereof, the method comprising: obtaining a sample comprising hematopoietic cells; removing PTPσ$^+$ cells from the sample; and implanting the sample into the subject.

The method may comprise contacting the sample with an anti-PTPσ antibody. For example, removing PTPσ$^+$ cells from the sample may comprise removing cells bound to the anti-PTPσ antibody from the sample. The anti-PTPσ antibody is labeled with a fluorophore and removing cells from the sample is accomplished by fluorescence activated cell sorting (FACs). In some embodiments, the anti-PTPσ antibody is labeled with a magnetic particle and removing cells from the sample comprises exposing the sample to a magnetic field (e.g., MACS). Those with skill in the art will recognize that an antibody may be labeled directly with a fluorophore or magnetic particle, for example, through a covalent bond, or through non-covalent interactions, for example, via a secondary antibody. In some embodiments, the anti-PTPσ antibody is immobilized on a surface and removing cells from the sample comprises separating the surface from the sample.

In some embodiments, the method comprises removing CD34$^-$, CD38$^+$, CD45RA$^+$, CD90$^-$, lin$^+$, Rho$^{hi}$, CD49f$^-$, and/or CD33$^+$ cells from the sample.

In some aspects, the invention relates to methods for producing a population of hematopoietic stem cells ("HSCs"), the method comprising: obtaining a sample comprising HSCs; sorting the cells in the sample based, at least in part, on their expression of PTPσ; and collecting the $PTP\sigma^-$ cells.

In some aspects, the invention relates to methods for implanting an effective amount of hematopoietic cells into a subject in need thereof, the method comprising: obtaining a sample comprising hematopoietic cells; sorting the cells in the sample based, at least in part, on their expression of PTPσ; collecting the $PTP\sigma^-$ cells; and implanting the $PTP\sigma^-$ cells into the subject.

The method may comprise contacting the sample with an anti-PTPσ antibody. For example, collecting the $PTP\sigma^-$ cells may comprise collecting the cells in the sample that do not bind to the anti-PTPσ antibody. Collecting the $PTP\sigma^-$ cells may be accomplished by fluorescence activated cell sorting. Similarly, collecting the $PTP\sigma^-$ cells may comprise exposing the sample to a magnetic field. In some embodiments, the anti-PTPσ antibody is immobilized on a surface and collecting the $PTP\sigma^-$ cells comprises separating the sample from the surface.

In certain embodiments, the method comprises collecting $PTP\sigma^-$ cells that are $CD34^+$, $CD38^-$, $CD45RA^-$, $CD90^+$, $lin^-$, $Rho^{lo}$, $CD49f^{+-}$, and/or $CD33^-$. For example, the method may comprise collecting $PTP\sigma^-CD34^+CD38^-$ $CD45RA^+$ $lin^-$ cells.

In some aspects, the invention relates to methods for preparing a sample of hematopoietic stem cells ("HSCs") for implantation, the method comprising contacting the sample with an inhibitor of the PTPσ pathway.

In some aspects, the invention relates to methods for implanting hematopoietic cells into a subject in need thereof, the method comprising: obtaining a sample comprising hematopoietic cells; contacting the sample with an inhibitor of the PTPσ pathway; and transplanting the sample into the subject.

The method may comprise removing $PTP\sigma^{+/+}$, $CD34^-$, $CD38^+$, $CD45RA^+$, $CD90^-$, $lin^+$, $Rho^{hi}$, $CD49f^-$, and/or CD33' cells from the sample. The method may comprise enriching the sample in $PTP\sigma^-$, $CD34^+$, $CD38^-$, $CD45RA^-$, $CD90^+$, $lin^-$, $Rho^{lo}$, $CD49f^{+-}$, and/or $CD33^-$ cells. For example, the method may comprise selecting $PTP\sigma^-CD34^+$ $CD38^-$ $CD45RA^+lin^-$ cells.

Methods Related to Inhibitors of a PTPσ Pathway

In some embodiments, the invention relates to methods for increasing a population of $PTP\sigma^-$ hematopoietic cells in a subject in need thereof, the method comprising administering to the subject an effective amount of an inhibitor of a PTPσ pathway.

In some embodiments, the invention relates to methods for promoting hematopoietic reconstitution in a subject in need thereof, the method comprising administering to the subject an inhibitor of a PTPσ pathway. The subject may have received an implant comprising hematopoietic cells, such as a transplant comprising hematopoietic cells. For example, the subject may require an allogeneic bone marrow transplantation. In some embodiments, the implant is a cord blood or bone marrow implant. In some embodiments, the method further comprises administering hematopoietic cells to the patient, e.g., before the subject receives the implant, simultaneously with the implant, and/or after the subject receives the implant.

In some embodiments, the subject has compromised hematopoietic function. For example, an inhibitor of a PTPσ pathway may be administered to accelerate the subject's own hematopoietic reconstitution process.

In some embodiments, the inhibitor is administered systemically. The inhibitor may accelerate hematologic recovery.

The subject may need hematopoietic reconstitution to counteract the effects of myelosuppressive therapy, e.g., because the subject has received myelosuppressive therapy. In some embodiments, the myelosuppressive therapy is chemotherapy. In some embodiments, the subject is a chemotherapy patient and the inhibitor is administered prior to administering the chemotherapy. In some embodiments, the subject is a chemotherapy patient and the inhibitor is administered concurrently with the chemotherapy. In some embodiments, the subject is a chemotherapy patient and the inhibitor is administered after administering the chemotherapy.

In other embodiments, the myelosuppressive therapy is radiation. In some embodiments, the inhibitor is administered prior to administering a radiation treatment. In some embodiments, the inhibitor is administered concurrently with radiation treatment. In some embodiments, the inhibitor is administered after administering radiation treatment.

In some embodiments, the subject has been exposed to radiation.

In some embodiments, the subject is a mammal. For example, the subject may be a mouse or a human.

This disclosure will be better understood from the Experimental Details which follow. However, one skilled in the art will readily appreciate that the specific methods and results discussed are merely illustrative of the disclosure as described more fully in the embodiments which follow thereafter.

EXEMPLIFICATION

Example 1—Methods

Animals—

Mice bearing constitutive deletion of PTPσ in Balb/c background are known in the art (Thompson K., et al., Mol Cell Neurosci.; 23(4):681-692 (2003)). Cby.SJL(B6)-Pt-$prc^a$/J (CD45.1 Balb/c) and NOD.Cg-$Prkdc^{scid}Il2rg^{tm1Wjl}$/SzJ (NSG) mice were obtained from Jackson Laboratory (Bar Harbor, Me.).

Statistical Analysis—

All data are shown as means±S.E.M using the Mann-Whitney test (two-tailed nonparametric analysis) and the 2-tailed Student's t test for the comparisons shown. $P<0.05$ was considered significant.

PTPσ Gene Expression Analysis in Murine Hematopoietic Cell Subsets

BM cells were sorted by FACS. Briefly, femurs were collected from 12-14 week female C57BL/6 ($CD45.2^+$) mice into IMDM with 10% FBS and 1% penicillin-streptomycin. Red blood cell lysis was performed using ACK Lysis buffer (Sigma Aldrich). Viable BM cells were quantified using Trypan blue, followed application of a lineage depletion column (Miltenyi Biotec, Auburn, Calif.). BM cells and lineage-depleted cells were isolated during the purification process. Cells were incubated with antibodies to c-Kit, Sca-1 and a lineage antibody cocktail (BD Biosciences, San Jose, Calif.) and sorted for the hematopoietic stem/progenitor cell subsets. cDNA was generated using RNeasy kit (Qiagen, Valencia, Calif.). Real-time PCR was performed using Taqman probes for glyceraldehyde-3-phosphate (GAPDH) and the various RPTPs (Applied Biosystems, Foster City, Calif.) according to the manufacturer's protocol.

Hematopoietic Progenitor Cell Assays

BM cells were collected as described above. Cells were then incubated with antibodies to c-Kit, Sca-1, a Lineage antibody, CD41, CD48 and CD150 (BD) to measure KSL and $SLAM^+KSL$ cells by flow cytometry. For CFCs, whole BM or Lineage-depleted cells were plated into methylcellulose (StemCell Technologies, Vancouver, BC, Canada), and colonies were scored on day 14. Complete blood counts were performed on a HemaVet 950 (Drew Scientific, Dallas, Tex.). Homing assays were performed with $Sca\text{-}1^+Lin^-$ BM cells. Briefly, $PTP\sigma^{+/+}$ or $PTP\sigma^{-/-}$ mice (CD45.2) were sorted by FACS for $Sca\text{-}1^+Lin^-$ BM cells ($9\times10^4$ cells per recipient mouse) and transplanted via tail-vein injection into lethally irradiated $CD45.1^+$ recipients. Donor cell homing to the BM was assessed at 18 hours post-transplant by flow cytometry.

Cell Cycle, Apoptosis and CXCR4 Expression Analysis

Cell cycle analysis and measurement of apoptosis were performed using flow cytometry. Briefly, BM cells were collected and stained for surface expression of ckit, sca-1 and lineage markers. Cells were then fixed with 2.5% paraformaldehyde and 2% FBS in 1× PBS and permeabilized with 0.25% saponin, 2% FBS in PBS and labeled with antibodies to Ki67-FITC (1% dilution, catalog number 556026, BD Biosciences) and 7-AAD (BD Biosciences). Analysis for apoptosis and necrosis was performed using the BD Annexin V Apoptosis Detection Kit Protocol (No. 556547, BD). For analysis of CXCR4 expression, murine BM cells were labeled with antibodies to ckit, sca-1 and lineage markers and CCXR4 (BD) and analyzed by flow cytometry. Human CB cells were lineage depleted and labeled with antibodies to CD34, CD38, CD45RA, PTPσ and CXCR4 (BD). Cells were then analyzed by flow cytometry.

shRNA Experiments and Rac1-GTP Analysis

BM KSL cells were cultured overnight in X-VIVO 15 serum-free media (Lonza, Basel Switzerland) with thrombopoietin (R & D), stem cell factor (R & D) and Flt-3 ligand (R & D), each at 100 ng/mL, and 50 uM 2-mercaptoethanol (Sigma Aldrich). Following overnight incubation, cells were treated with 10 ug/mL polybrene (Sigma Aldrich) and transduced with a PTPσ-lentiviral shRNA or a scrambled lentiviral vector expressing green fluorescent protein (GFP) under the control of a murine stem cell virus (MSCV) promoter for an additional 48 hours. $GFP^+$ cells were isolated by FACS and re-stained for KSL. Cells were then fixed in 4% paraformaldehyde, permeabilized with 0.25% saponin in PBS and stained with a 1% solution of Rac1-GTP antibody (NewEast Biosciences, King of Prussia, Pa.), followed by flow cytometric analysis.

CAFC and Transendothelial Migration Assays

CAFCs were performed as follows. M2-10B4 stromal cells were cultured to confluence in 96-well flat bottom plates and irradiated at 4000 cGy. At 24 hours post irradiation, wells were seeded with dilutions of BM cells from $PTP\sigma^{+/+}$ or $PTP\sigma^{-/-}$ mice (81,000-333 cells per well). CAFCs were scored at week 5.

Transendothelial migration assays were performed as follows. VeraVec™ mouse spleen endothelial cells (Angiocrine Bioscience, New York N.Y.) were cultured to confluence in 8 μM pore transwells (Corning Incorporated, Corning N.Y.). Transwells were seeded with 200,000 BM cells in IMDM with 10% FBS, 1% penicillin-streptomycin, 125 ng/mL stem cell factor, 50 ng/mL Flt-3 ligand and 20 ng/mL thrombopoietin with or without 25 μM Rac inhibitor, EHT1864 (R&D Systems, Minneapolis, Minn.). 100 ng/mL SDF-1α (R&D) or media was added to the bottom chamber of the transwell. 16 hours post culture, cells in the bottom chamber were collected and CFCs were set up with the migrated cells.

Cell Cycle Analysis

For cell cycle analysis, BM was immunostained for KSL cells and the cells were then fixed with 2.5% paraformaldehyde in 2% FBS. Cells were permeabilized with 0.25% saponin (Calbiochem, La Jolla, Calif.) and labeled with antibodies to Ki67-FITC and 7-AAD (BD).

Competitive Repopulation Assays

BM cells from $PTP\sigma^{+/+}$ or $PTP\sigma^{-/-}$ mice (CD45.2), along with $2\times10^5$ BM competitor cells (CD45.1) were injected via tail-vein into lethally irradiated (700-800 cGy), congenic CD.45.1 Balb/c mice. Multi-lineage hematopoietic reconstitution in the PB was measured at 4-16 weeks post-transplant by flow cytometry. Animals were considered to be engrafted if ≥1% donor $CD45.2^+$ cells were detected. BM cells of recipient mice were also analyzed at 16 weeks by flow cytometry. Secondary competitive repopulation assays were performed using BM cells from primary mice, as previously described.

Human Cord Blood Transplantation Assays

For the xenotransplantation assays into NSG mice, human CB cells were FACS-sorted for $CD34^+CD38^-CD45RA^-Lin^-$ cells, $CD34^+CD38^-CD45RA^-Lin^-PTP\sigma^-$ cells or $CD34^+CD38^-CD45RA^-Lin^-PTP\sigma^+$ cells. 200 purified cells were transplanted via intrafemoral injections in 8-12 week old female NSG recipients preconditioned with 275 cGy. Prior to transplantation, NSG mice were anesthetized using 20 mg/mL Avertin (Sigma-Aldrich). Engraftment was monitored in the PB as described above. Mice were considered as engrafted if ≥0.5% human $CD45^+$ cells were detected in the bone marrow of NSG recipients.

Example 2—PTPσ Expression

CD45, PTPσ and PTP-epsilon (PTPε) were expressed at >100-fold higher levels in BM $ckit^+sca\text{-}1^+lin^-$ (KSL) stem/progenitor cells compared to other receptor PTPs, including PTPζ (FIG. 1A). PTPσ expression was increased significantly in HSCs compared to more mature hematopoietic cell populations (FIG. 1A).

Example 3—Hematopoietic Cells from $PTP\sigma^{-/-}$ Mice

Figure 1B:
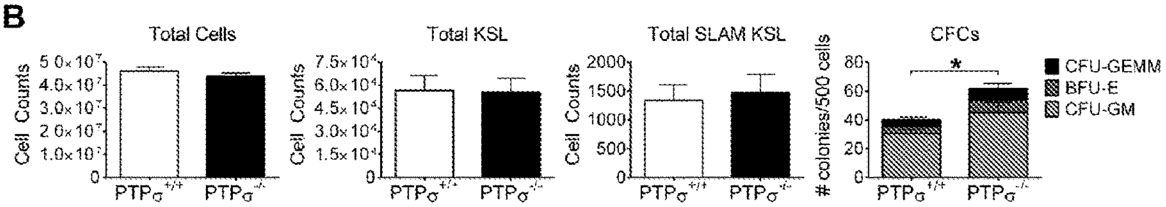
Figure 1C:
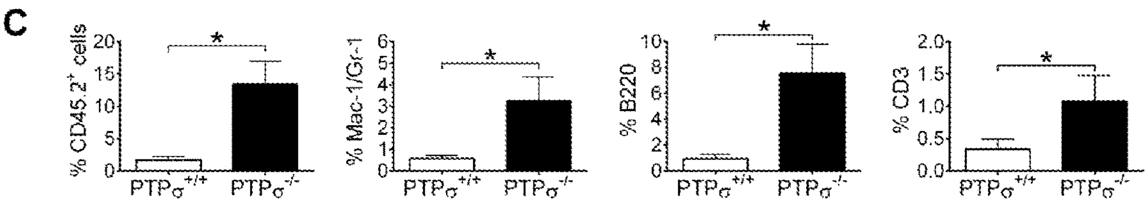
Figure 1D:
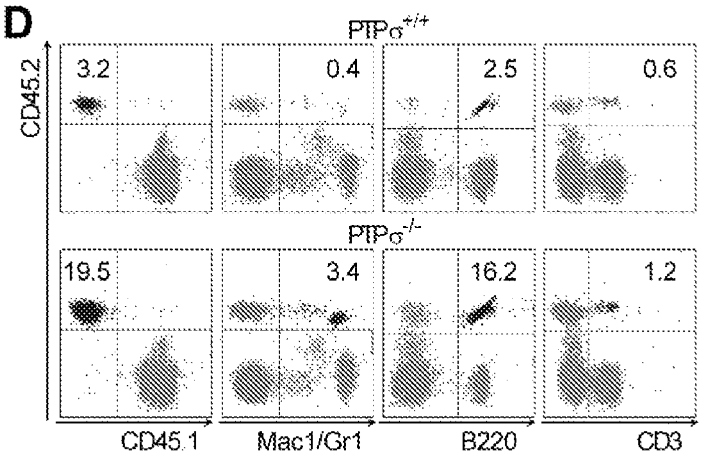
Figure 1E:
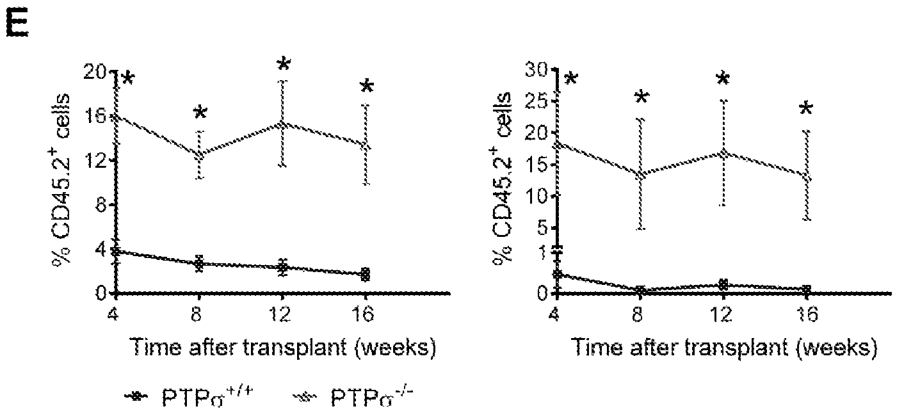
Figure 2A:
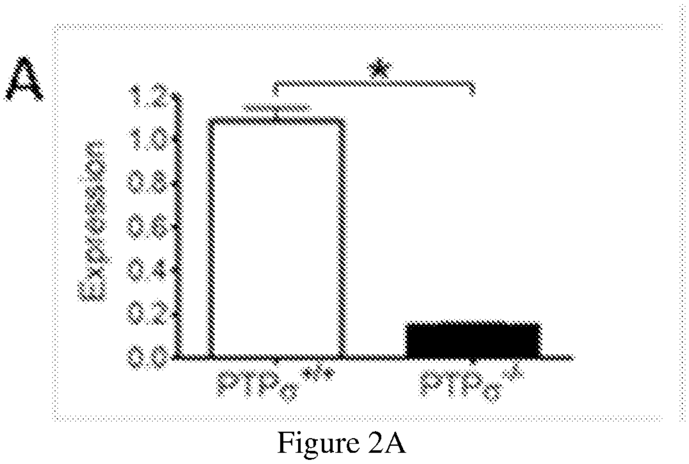
FIG. 2. Baseline hematologic profile of adult $PTP\sigma^{-/-}$ mice versus $PTP\sigma^{+/+}$ mice. (2A) Expression of PTPσ in BM KSL cells in $PTP\sigma^{+/+}$ and $PTP\sigma^{-/-}$ mice by qRT-PCR (n=6/group, *P<0.0001). (2B) Peripheral blood complete blood counts in 8-12 week old $PTP\sigma^{+/+}$ and $PTP\sigma^{-/-}$ mice (n=6-14 mice/group). (2C) Representative flow cytometric analysis of BM KSL cells and $SLAM^+$KSL cells in $PTP\sigma^{+/+}$ and $PTP\sigma^{-/-}$ mice. Numbers represent the percentages of KSL cells and $CD150^+CD41/48^-$KSL cells in each group. (2D) Mean numbers of total BM cells, KSL cells, $SLAM^+$ KSL cells in $PTP\sigma^{+/+}$ and $PTP\sigma^{-/-}$ mice are shown (±SEM, n=6). (2E) Cell cycle analysis of BM KSL cells from $PTP\sigma^{+/+}$ and $PTP\sigma^{-/-}$ mice is shown. Mean values+/−SEM (n=5/group). (2F) Mean levels of apoptotic cells (Annexin $V^+/7AAD^-$) and necrotic cells (Annexin $V^+/7AAD^+$) are shown (n=7). (2G) Mean percentage donor $CD45.2^+$ cell engraftment is shown at 18 hours post-injection of $9\times10^4$ BM Sca-$1^+lin^-$ cells from $PTP\sigma^{+/+}$ and $PTP\sigma^{-/-}$ mice into $CD45.1^+$ recipients (n=4/group).
Figure 2B:
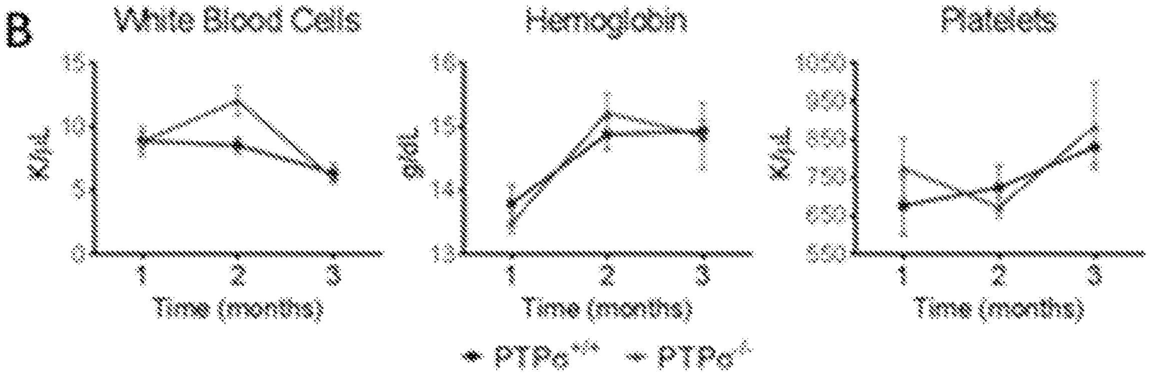
Figure 2C:
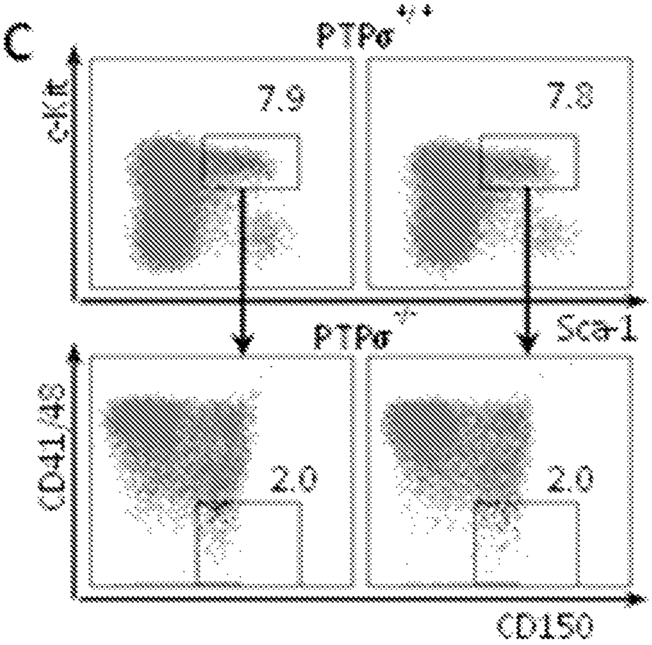
Figure 2D:
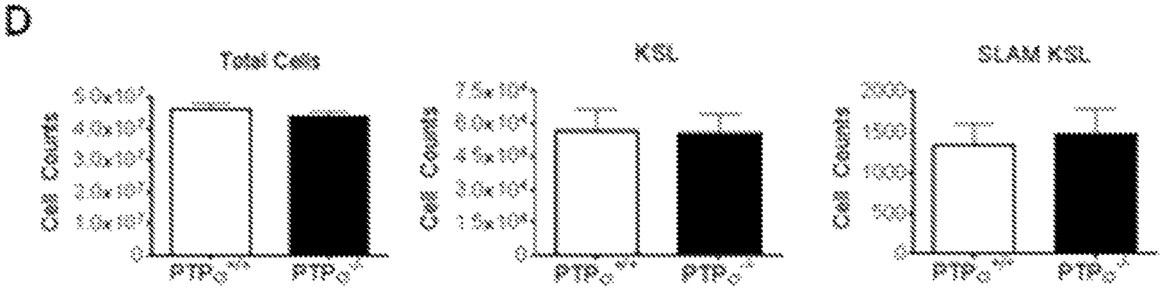
Figure 2E:
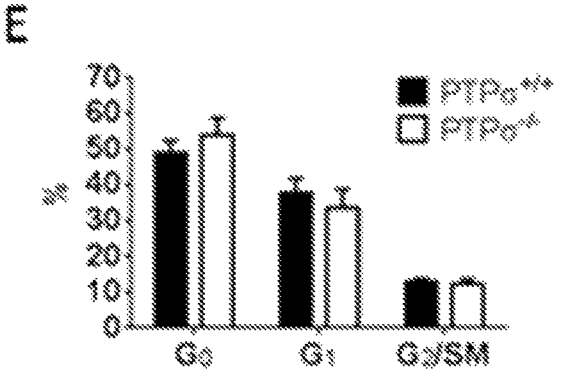
Figure 2F:
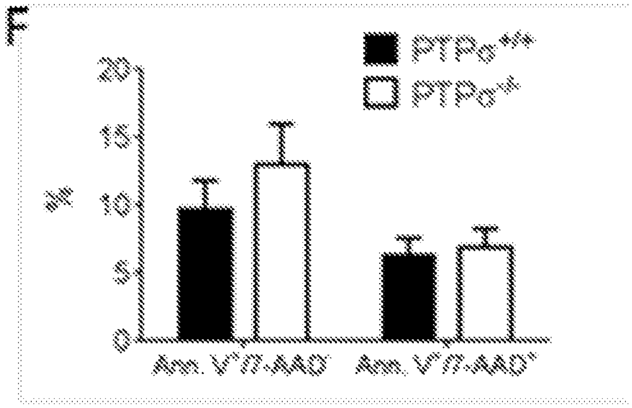
Figure 2G:
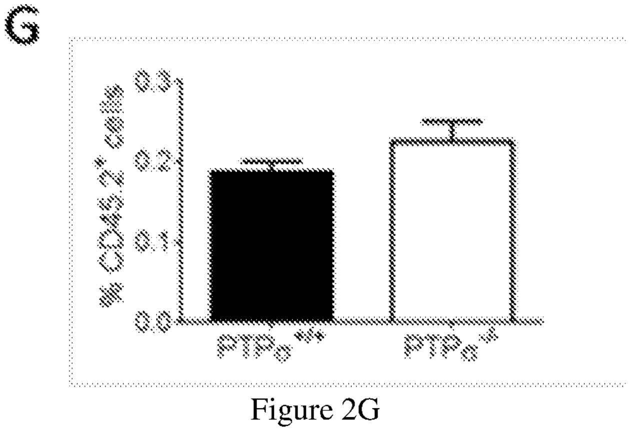

In order to determine if PTPσ had a functional role in regulating HSC fate, the hematopoietic phenotype and function of $PTP\sigma^{-/-}$ mice and $PTP\sigma^{+/+}$ mice were compared. $PTP\sigma^{-/-}$ mice were viable and displayed decreased PTPσ expression in BM $lin^-$ cells from $PTP\sigma^{-/-}$ mice (FIG. 2). Adult $PTP\sigma^{-/-}$ mice had normal peripheral blood counts and no alterations in total BM cells, KSL cells, $SLAM^+KSL$ HSCs, HSC cell cycle status or apoptosis compared to $PTP\sigma^{+/+}$ mice (FIG. 2). However, $PTP\sigma^{-/-}$ mice contained significantly increased myeloid colony forming cells (CFCs) compared to $PTP\sigma^{+/+}$ mice (FIG. 1B). Furthermore, mice which were competitively transplanted with limiting doses of BM cells from $PTP\sigma^{-/-}$ mice had 8-fold increased donor $CD45.2^+$ hematopoietic cell engraftment at 16 weeks compared to mice transplanted with the identical cell dose from $PTP\sigma^{+/+}$ mice (FIG. 1C). Reconstitution of myeloid, B cell and T cell lineages was also significantly increased in mice transplanted with $PTP\sigma^{-/-}$ BM cells compared to recipients of $PTP\sigma^{+/+}$ cells (FIG. 1C,D). Secondary competitive transplantation assays demonstrated that $PTP\sigma^{-/-}$ donor BM cells contained significantly increased long-term HSC function compared to BM cells from PTPσ$^{+/+}$ mice (FIG. 1E). Of note, we observed no differences in the homing capacity of donor BM cells from PTPσ$^{-/-}$ mice versus PTPσ$^{+/+}$ mice (FIG. 2).

Example 4—PTPσ Signaling Pathway

Figure 3A:
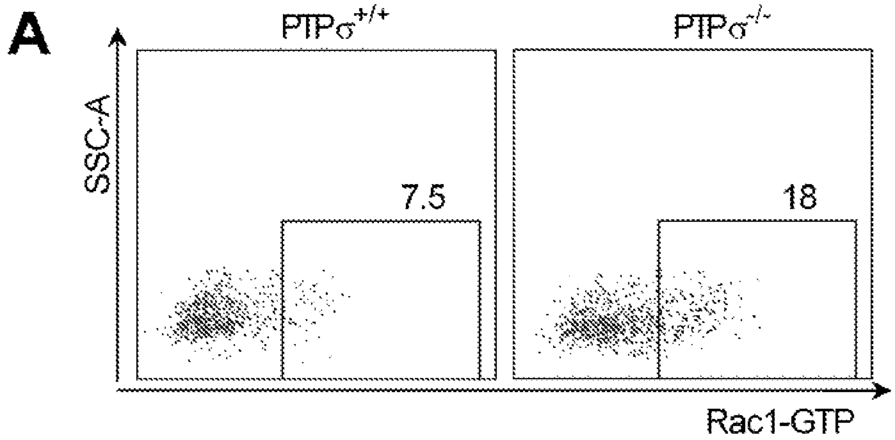
FIG. 3. PTPσ regulates Rac1 activation in HSCs and Rac1 inhibition abrogates the $PTP\sigma^{-/-}$ BM cell migration capacity. (3A) At left, flow cytometric analysis of Rac1-GTP levels in BM KSL cells from $PTP\sigma^{+/+}$ and $PTP\sigma^{+/+}$ mice is shown. Numbers represent the percentages of Rac1-$GTP^+$ cells. At right, mean percentages of Rac1-$GTP^+$KSL cells are shown in $PTP\sigma^{-/-}$ and $PTP\sigma^{+/+}$ mice. *P=0.008 (n=3, t test). (3B) At left, flow cytometric analysis of Rac1-GTP levels in wild type BM KSL cells treated with scramble-shRNA or PTPσ-shRNA is shown. Numbers represent the percentages of Rac-1 $GTP^+$ cells. At right, scatter plot of percent Rac1-$GTP^+$KSL cells is shown in each group. Horizontal bars represent mean values. *P=0.01 (n=6, t test). (3C) Poisson statistical analysis of a limiting dilution assay of 5-week CAFCs in $PTP\sigma^{-/-}$ versus $PTP\sigma^{+/+}$ BM cells. The CAFC frequency for $PTP\sigma^{-/-}$ BM cells was 1 in 839 cells versus 1 in 3,801 cells for $PTP\sigma^{+/+}$ BM cells (n=10/group, P=0.0001) (3D) Mean numbers of CFCs are shown from the lower chambers of transendothelial migration assays containing $PTP\sigma^{+/+}$ BM cells, $PTP\sigma^{-/-}$ BM cells, treated with and without EHT1864. *P<0.0001 (n=12, t test) for total CFCs; **P<0.0001 for total CFCs (n=6, t test).
Figure 3B:
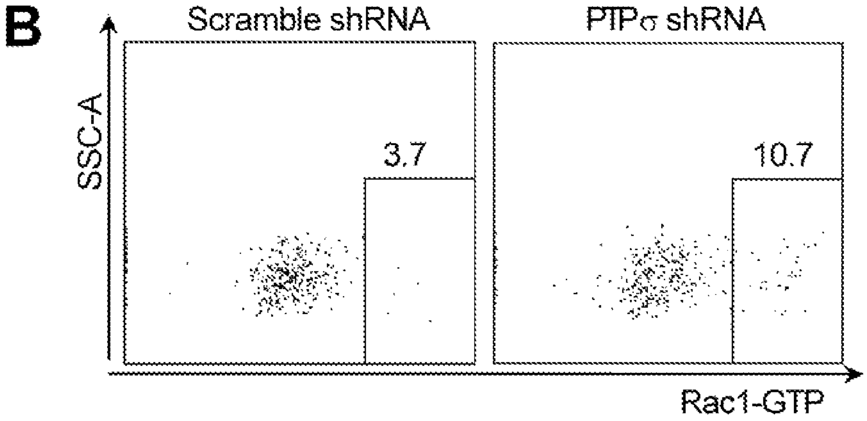
Figure 3C:
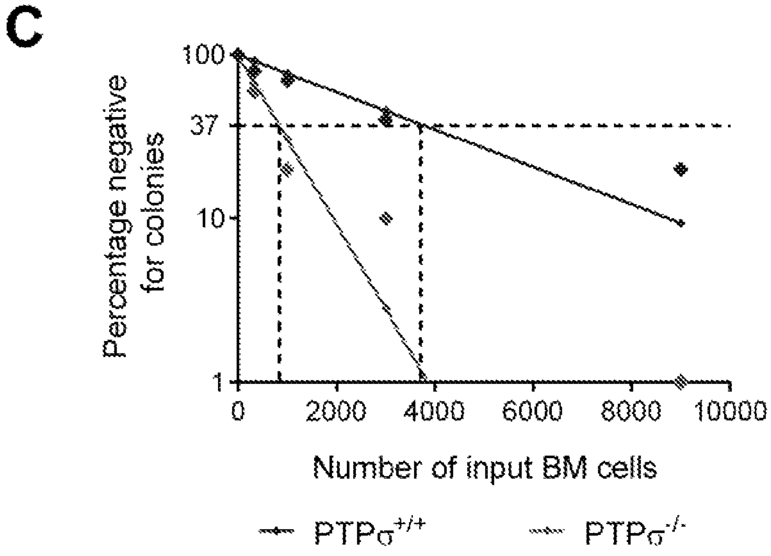
Figure 3D:
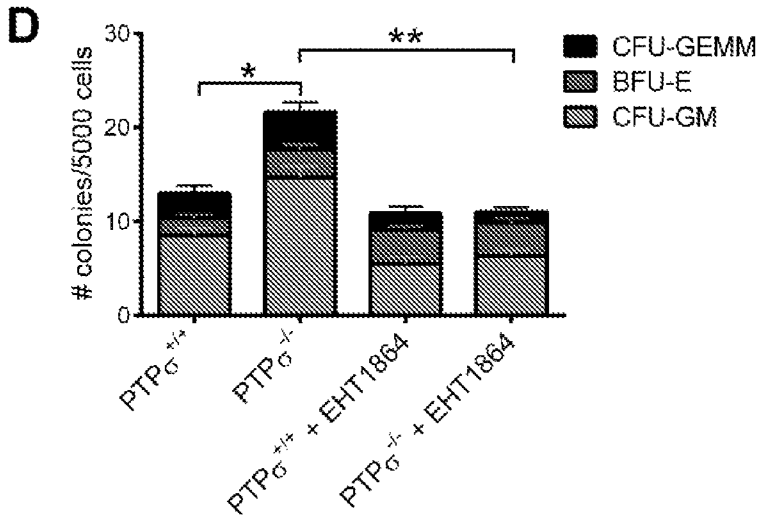
Figure 4:
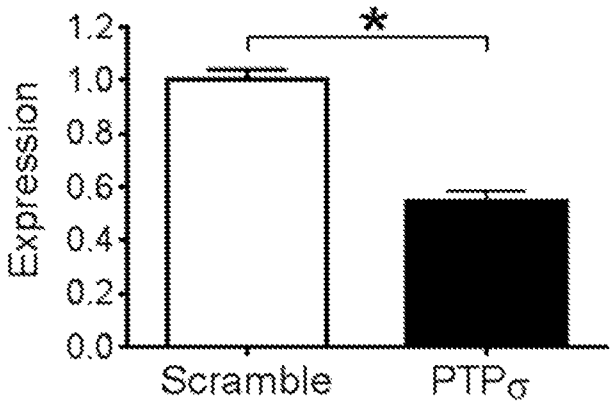
FIG. 4. Expression of PTPσ in BM KSL cells at 48 hours after treatment with PTPσ-shRNA (PTPσ) or scramble shRNA (n=6/group), *P<0.0001.

Since PTPσ$^{-/-}$ HSCs displayed increased repopulating capacity in vivo compared to PTPσ$^{+/+}$ HSCs, this suggested that PTPσ might regulate processes involved in HSC engraftment or self-renewal, such as Rac proteins, a subset of RhoGTPases, which are necessary for normal HSC engraftment capacity. In cell lines, PTPσ dephosphorylates and thereby activates p250GAP, a RhoGTPase which inhibits Rac protein activation. Rac1-GTP, the activated form of Rac1, was significantly increased in BM KSL cells from PTPσ$^{-/-}$ mice compared to PTPσ$^{+/+}$ mice (FIG. 3A). Treatment of wild type BM KSL cells with PTPσ-shRNA also significantly increased Rac1-GTP levels compared to scramble-shRNA treated BM KSL cells, demonstrating a molecular link between PTPσ and Rac1 (FIG. 3B, FIG. 4). Deletion of Rac1 and Rac2 has been previously shown to decrease the trans-endothelial migration capacity and cobblestone area forming cell (CAFC) content of BM cells compared to control BM cells. Similarly, PTPσ$^{-/-}$ BM cells had 4-fold increased numbers of 5-week CAFCs compared to PTPσ$^{+/+}$ BM cells (FIG. 3C). Furthermore, PTPσ$^{-/-}$ BM cells displayed significantly increased trans-endothelial cell migration capacity compared to PTPσ$^{+/+}$ BM cells (FIG. 3D). Treatment of PTPσ$^{-/-}$ BM cells with EHT1864, a Rac inhibitor, completely abrogated the transendothelial migration capacity of PTPσ$^{-/-}$ cells (FIG. 3D).

Example 5—Negative Selection of HSCs for PTPσ Expression

Figure 5A:
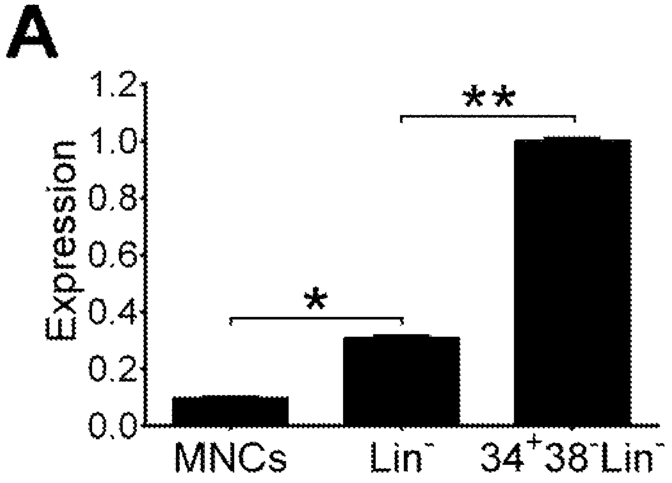
FIG. 5. Selection of $PTP\sigma^-$ CB cells enriches for human HSCs. (5A) Mean expression of PTPσ in subsets of CB cells by qRTPCR. *P<0.0001, **P<0.0001 (n=3, t test). (5B) Flow cytometric analysis is shown of PTPσ expression on CB cells and on CB $CD34^+CD38^-CD45RA^-lin^-$ cells. Numbers represent percentage PTPσ levels. (5C) Mean levels of human $CD45^+$ hematopoietic cell and multilineage engraftment in the PB of NSG mice at 16 weeks following intrafemoral injection of human CB $CD34^+CD38^-CD45RA^-lin^-$ cells ($34^+38RA^-$), $CD34^+CD38^-CD45RA^-lin^-PTP\sigma^+$ cells ($34^+38RA^-PTP\sigma^+$) or $CD34^+CD38^-CD45RA^-lin^-PTP\sigma^-$ cells ($34^+38^-RA^-PTP\sigma^+$. % Human $CD45^+$: *P=0.0002, **P<0.0001; % $CD13^+$: *P<0.0001, **P<0.0001; % $CD19^+$: *P=0.0002, **P<0.0001; % $CD3^+$: *P<0.0001, **P<0.0001 (n=11-18/group, Mann-Whitney). (5D) Flow cytometric analysis of human $CD45^+$ cell and multilineage engraftment is shown at 16 weeks in the PB of mice transplanted with CB $34^+38^-RA^-$ cells or $34^+38^-RA^-PTP\sigma^-$ cells. Numbers represent the percentages of donor lineage cells. (5E) Mean levels of human $CD45^+$ cell engraftment are shown over time post-transplant in the PB of NSG mice transplanted with parent $34^+38^-RA^-$ cells, $34^+38^-RA^-PTP\sigma^+$ or $34^+38^-RA^-PTP\sigma^-$ cells. 8 weeks: *P=0.002 ($PTP\sigma^-$ vs. parent), ^P<0.0001 ($PTP\sigma^-$ vs. $PTP\sigma^+$); 12 weeks: *P=0.002, ^P<0.0001; 16 weeks: *P=0.0002, ^P<0.0001 (n=11-18/group).
Figure 5B:
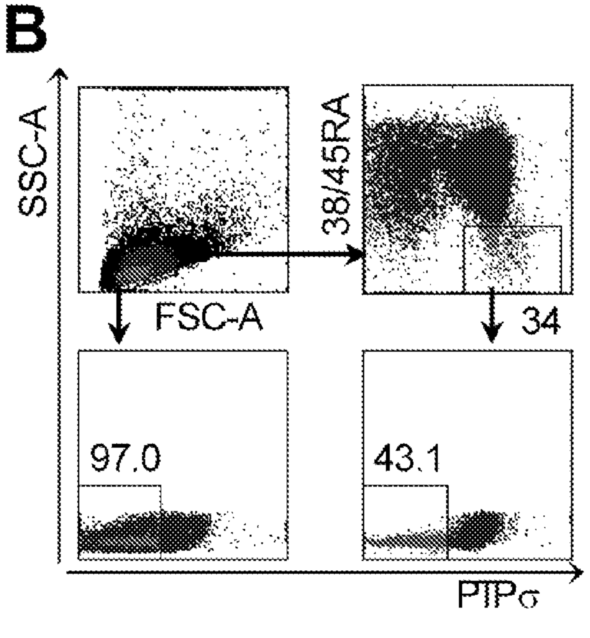
Figure 5C:
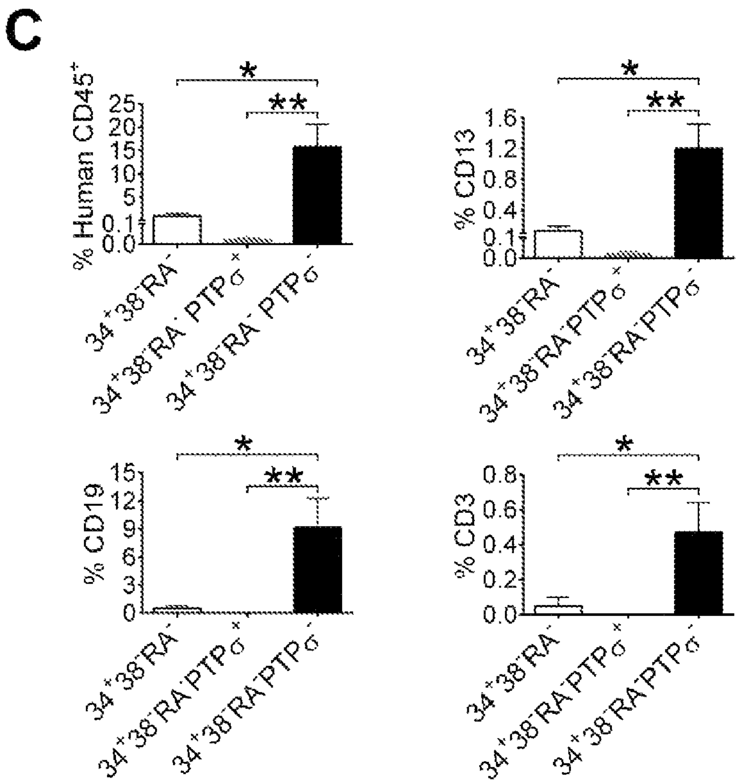
Figure 5D:
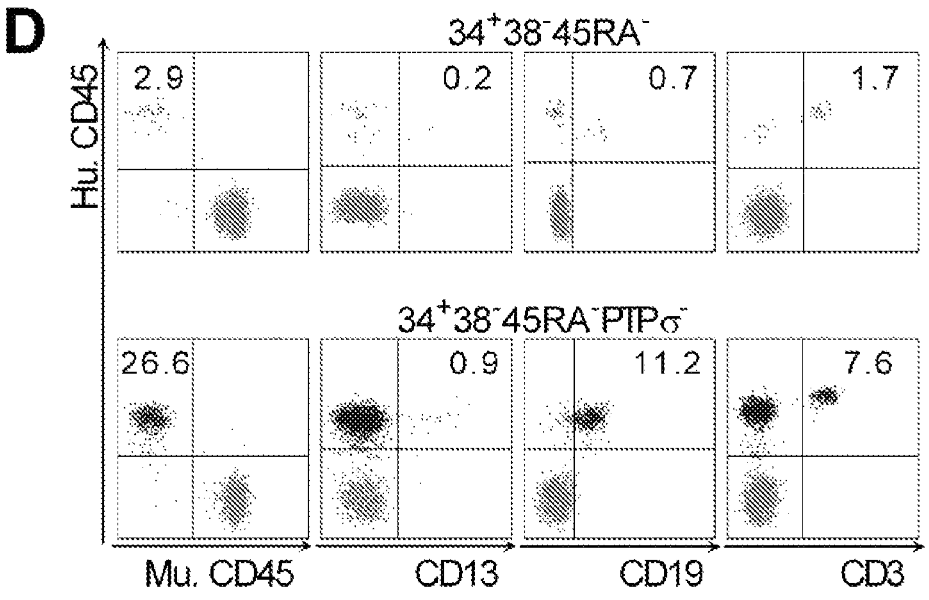
Figure 5E:
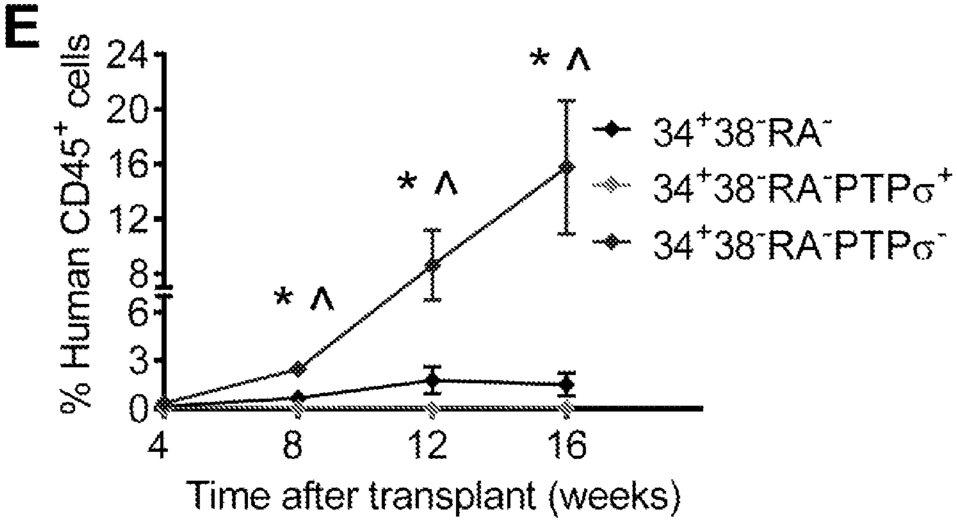
Figure 6A:
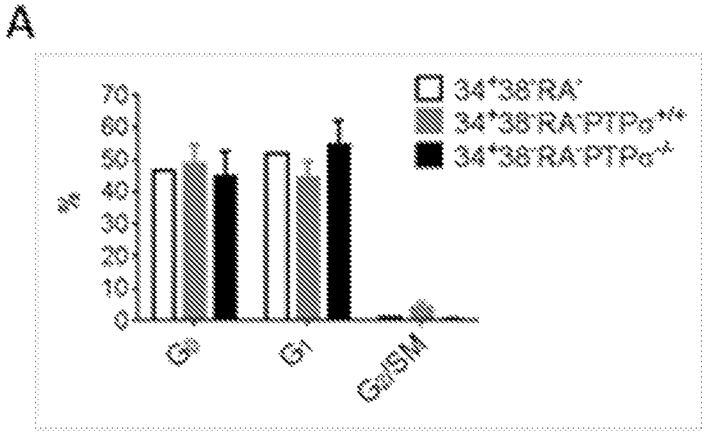
FIG. 6. Cell cycle status and CXCR4 expression on human CB cells based on PTPσ expression. (6A) Mean percentages of cells in $G_0$, $G_1$ and $G_2$SM phase of cell cycle within the cell populations shown (n=5). (6B) Representative flow cytometric analysis of surface CXCR4 expression on the human CB cell populations shown. Numbers represent the percentages of $CXCR4^+$ cells in each group. (6C) The scatter plot shows % $CXCR4^+$ cells within CB $CD34^+CD38^-CD45RA^-lin^-$ cells ($34^+38^-RA^-$), $CD34^+CD38^-CD45RA^-lin^-PTP\sigma^+$ cells ($34^+38^-RA^-PTP\sigma^+$) or $CD34^+CD38^-CD45RA^-lin^-PTP\sigma^+$ cells ($34^+38^-RA^-PTP\sigma^+$). Horizontal bars represent mean values for each group. *P=0.01, **P=0.01 (n=6/group, t test)
Figure 6B:
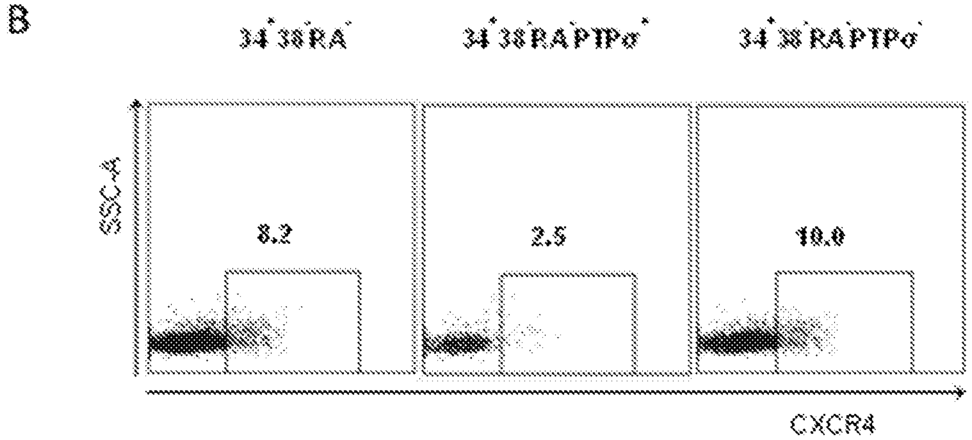
Figure 6C:
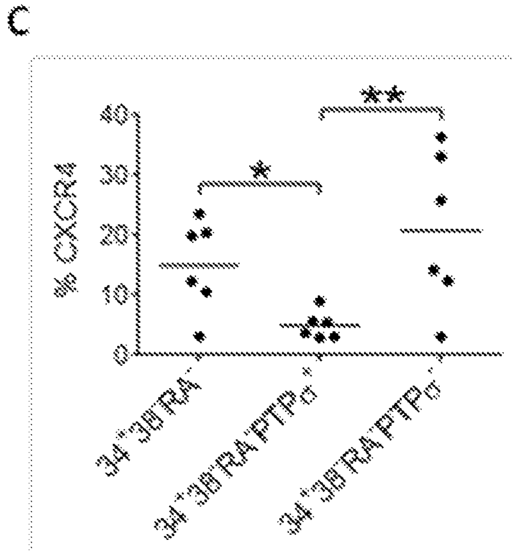

PTPσ was expressed by a mean of 49.9% of human CB $CD34^+CD38^-lin^-$ stem/progenitor cells (n=6, FIGS. 5A, 5B). The transplantation assays were performed into NOD/SCID-IL2Receptor-gamma chain null (NSG) mice to assess the repopulating capacity of CB HSCs selected for PTPσ expression. At 16 weeks after transplant, NSG mice transplanted with $CD34^+CD38^-CD45RA^-lin^-PTP\sigma^-$ cells displayed 15-fold higher engraftment compared to mice transplanted with parent $CD34^+CD38^-CD45RA^-lin^-$ cells and more than 15-fold higher compared to mice transplanted with $CD34^+CD38^-CD45RA^-lin^-PTP\sigma^+$ cells (FIG. 5C). NSG mice transplanted with $CD34^+CD38^-CD45RA^-lin^-PTP\sigma^-$ cells had significantly increased engraftment of donor myeloid cells, B cells and T cells compared to mice transplanted with $CD34^+CD38^-CD45RA^-lin^-$ cells or $CD34^+CD38^-CD45RA^-lin^-PTP\sigma^+$ cells (FIG. 5C, 5D). Temporally, the engraftment of PTPσ$^-$ CB cells significantly increased between 8 to 16 weeks compared to parent CB cells or PTPσ$^+$ CB cells (FIG. 5E). Of note, $CD34^+CD38^-CD45RA^-lin^-PTP\sigma^-$ cells displayed no difference in cell cycle status compared to $CD34^+CD38^-CD45RA^-lin^-$ cells or $CD34^+CD38^-CD45RA^-lin^-PTP\sigma^+$ cells (FIG. 6). Surface expression of CXCR4, the CXC chemokine receptor type 4, which regulates HSC homing and retention in the BM microenvironment, was not different between $CD34^+CD38^-CD45RA^-lin^-$ cells and $CD34^+CD38^-CD45RA^-lin^-PTP\sigma^-$ cells, but both populations had higher CXCR4 expression compared to $CD34^+CD38^-CD45RA^-lin^-PTP\sigma^+$ cells (FIG. 6). No differences in CXCR expression between BM KSL cells from PTPσ$^{-/-}$ mice and PTPσ$^{+/+}$ mice were found (mean 2.7% $CXCR4^+$ vs. 3.2%, respectively, n=6).

It will be understood by one of ordinary skill in the art that the compositions and methods described herein may be adapted and modified as is appropriate for the application being addressed and that the compositions and methods described herein may be employed in other suitable applications, and that such other additions and modifications will not depart from the scope hereof. The disclosure contemplates all uses of the agents and compositions of the disclosure, including their use in therapeutic methods, in diagnostic assays, and their use as research tools.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for implanting hematopoietic cells into a subject in need thereof, the method comprising:

obtaining a sample comprising hematopoietic cells;

contacting the sample with an inhibitor of the PTPσ pathway; and transplanting the sample into the subject.

2. The method of claim 1, wherein the inhibitor of the PTPσ pathway is a p250GAP antagonist.

3. The method of claim 1, wherein the inhibitor of the PTPσ pathway is a Rac1 agonist.

4. The method of claim 1, wherein the inhibitor of the PTPσ pathway is a small molecule or an interfering nucleic acid.

5. The method of claim 1, wherein the method comprises removing PTPσ$^+$, $CD34^-$, $CD38^+$, $CD45RA^+$, $CD90^-$, $lin^+$, $Rho^{hi}$, $CD49f^-$, and/or $CD33^+$ cells from the sample.

6. The method of claim 1, wherein the method comprises enriching the sample in PTPσ$^-$, $CD34^+$, $CD38^-$, $CD45RA^-$, $CD90^+$, $lin^-$, $Rho^{lo}$, $CD49f^{+-}$, and/or $CD33^-$ cells.

7. The method of any one of claim 1, wherein the inhibitor of the PTPσ pathway is an interfering nucleic acid.

8. The method of claim 7, wherein the inhibitor of the PTPσ pathway is an shRNA.

9. A method for promoting hematopoietic reconstitution in a subject in need thereof, the method comprising administering to the subject an inhibitor of a PTPσ pathway, wherein the subject has received an implant comprising hematopoietic cells, or wherein the method further comprises administering hematopoietic cells to the patient before the subject receives the PTPσ pathway inhibitor, simultaneously with the PTPσ pathway inhibitor, or after the subject receives the PTPσ pathway inhibitor.

10. The method of claim 9, wherein the subject has compromised hematopoietic function.

11. The method of claim 9, wherein the inhibitor of the PTPσ pathway is a PTPσ inhibitor.

12. The method of claim 9, wherein the inhibitor of the PTPσ pathway is a p250GAP antagonist.

13. The method of claim 9, wherein the inhibitor of the PTPσ pathway is a Rac1 agonist.

14. The method of claim 9, wherein the inhibitor of the PTPσ pathway is a small molecule or an interfering nucleic acid.

* * * * *